US012440374B2

(12) United States Patent
Clauson et al.

(10) Patent No.: US 12,440,374 B2
(45) Date of Patent: Oct. 14, 2025

(54) MECHANICAL HOLE PUNCH FOR THE REDUCTION OF INTRAOCULAR PRESSURE AND METHODS OF USE

(71) Applicant: Innovative Drive Corporation, Reno, NV (US)

(72) Inventors: Luke W. Clauson, Reno, NV (US); Matthew B. Newell, Reno, NV (US)

(73) Assignee: Innovative Drive Corporation, Reno, NV (US)

(*) Notice: Subject to any disclaimer, the term of this patent is extended or adjusted under 35 U.S.C. 154(b) by 356 days.

(21) Appl. No.: 18/153,820

(22) Filed: Jan. 12, 2023

(65) Prior Publication Data

US 2023/0218439 A1 Jul. 13, 2023

Related U.S. Application Data

(60) Provisional application No. 63/266,720, filed on Jan. 12, 2022.

(51) Int. Cl.
*A61F 9/007* (2006.01)

(52) U.S. Cl.
CPC ...... *A61F 9/00763* (2013.01); *A61F 9/00781* (2013.01)

(58) Field of Classification Search
CPC .............. A61F 9/00763; A61F 9/00781; A61F 2009/00868; A61F 2009/00891
See application file for complete search history.

(56) References Cited

U.S. PATENT DOCUMENTS 2,598,060 A 5/1952 Kadesky
2,838,050 A 6/1958 Ara
3,074,407 A 1/1963 Moon et al.
3,844,272 A 10/1974 Banko
(Continued)

FOREIGN PATENT DOCUMENTS

EP 0010321 A1 4/1980
EP 1615604 B1 8/2009
(Continued)

OTHER PUBLICATIONS

U.S. Appl. No. 17/716,884, filed Apr. 8, 2022, US 2022-0323254.
U.S. Appl. No. 18/072,389, filed Nov.. 30, 2022, US 2023-0165715.

*Primary Examiner* — Julian W Woo
(74) *Attorney, Agent, or Firm* — Mintz Levin Cohn Ferris Glovsky and Popeo, P.C.

(57) ABSTRACT

A device to treat an ocular condition having a rotary housing located within an outer housing rotationally fixed to a rotary spindle and rotationally movable relative to the outer housing; an elongate shaft projecting distally from the distal end region of the outer housing along a central longitudinal axis, at least a distal end region of the elongate shaft being sized for insertion into an eye. The elongate shaft includes an outer shaft and an inner cutting tube. Upon actuation of the device, the rotary housing rotates causing the rotary spindle and the inner cutting tube to rotate around the central longitudinal axis while simultaneously causing axial extension of the inner cutting tube distally along the central longitudinal axis to advance the distal cutting surface through a target tissue forming a tissue slug. Related devices, systems, and methods are provided.

28 Claims, 15 Drawing Sheets

(56) References Cited

U.S. PATENT DOCUMENTS

| | | | | |
|---|---|---|---|---|
| 4,108,182 | A * | 8/1978 | Hartman | A61F 9/00763 606/171 |
| 4,263,899 | A | 4/1981 | Burgin | |
| 4,600,014 | A | 7/1986 | Beraha | |
| 4,672,965 | A | 6/1987 | Baum | |
| 4,900,300 | A | 2/1990 | Lee | |
| 4,907,599 | A | 3/1990 | Taylor | |
| 5,423,330 | A | 6/1995 | Lee | |
| 5,476,099 | A | 12/1995 | Robinson et al. | |
| 5,507,298 | A | 4/1996 | Schramm et al. | |
| 5,827,316 | A | 10/1998 | Young et al. | |
| 6,080,173 | A | 6/2000 | Williamson, IV et al. | |
| 6,428,555 | B1 | 8/2002 | Koster, Jr. | |
| 6,869,398 | B2 | 3/2005 | Obenchain et al. | |
| 7,094,225 | B2 | 8/2006 | Tu et al. | |
| 7,713,228 | B2 | 5/2010 | Robin | |
| 7,819,298 | B2 | 10/2010 | Hall et al. | |
| 8,267,882 | B2 | 9/2012 | Euteneuer et al. | |
| 8,303,519 | B2 | 11/2012 | Yunoki et al. | |
| 8,491,549 | B2 | 7/2013 | Conston et al. | |
| 8,894,603 | B2 | 11/2014 | Badawi et al. | |
| 9,107,729 | B2 | 8/2015 | Sorensen et al. | |
| 9,572,963 | B2 | 2/2017 | Tu et al. | |
| 9,597,230 | B2 | 3/2017 | Haffner et al. | |
| 9,795,503 | B2 | 10/2017 | Perez Grossmann | |
| 9,855,167 | B2 | 1/2018 | Badawi et al. | |
| 9,895,258 | B2 | 2/2018 | Badawi et al. | |
| 9,956,116 | B2 | 5/2018 | Grover et al. | |
| 10,123,905 | B2 | 11/2018 | Mittelstein et al. | |
| 10,179,066 | B2 | 1/2019 | Badawi et al. | |
| 10,213,107 | B2 | 2/2019 | Cao et al. | |
| 10,357,274 | B2 | 7/2019 | Pandey et al. | |
| 10,368,899 | B2 | 8/2019 | Pandey | |
| 10,390,993 | B1 | 8/2019 | Berlin | |
| 10,406,030 | B2 | 9/2019 | Badawi et al. | |
| 10,463,385 | B2 | 11/2019 | Ichikawa | |
| 10,485,579 | B2 | 11/2019 | Lenker | |
| 10,653,558 | B2 | 5/2020 | Kahook et al. | |
| 10,729,582 | B2 | 8/2020 | Biancalana et al. | |
| 10,744,033 | B2 | 8/2020 | Baerveldt et al. | |
| 10,786,391 | B2 | 9/2020 | Kahook | |
| 10,828,473 | B2 | 11/2020 | Haffner et al. | |
| 10,857,027 | B2 | 12/2020 | Badawi et al. | |
| 10,905,591 | B1 | 2/2021 | Ianchulev | |
| 10,918,521 | B2 | 2/2021 | Grover et al. | |
| 11,076,989 | B2 | 8/2021 | Kahook | |
| 11,090,188 | B2 | 8/2021 | Badawi et al. | |
| 11,116,660 | B2 | 9/2021 | Badawi et al. | |
| 11,147,709 | B2 | 10/2021 | Kahook et al. | |
| 11,166,847 | B2 | 11/2021 | Badawi et al. | |
| 2002/0151835 | A1 | 10/2002 | Ross | |
| 2007/0073275 | A1 | 3/2007 | Conston et al. | |
| 2008/0114364 | A1 | 5/2008 | Goldin et al. | |
| 2009/0287233 | A1 | 11/2009 | Huculak | |
| 2011/0077626 | A1 | 3/2011 | Baerveldt et al. | |
| 2012/0330101 | A1 | 12/2012 | Brennan et al. | |
| 2014/0288499 | A1 | 9/2014 | Miller | |
| 2017/0303940 | A1 | 10/2017 | Sperry et al. | |
| 2018/0289544 | A1 | 10/2018 | Baerveldt et al. | |
| 2019/0038462 | A1 | 2/2019 | Vandiest et al. | |
| 2020/0281766 | A1 | 9/2020 | Berlin | |
| 2020/0390600 | A1 | 12/2020 | Perera et al. | |
| 2021/0022919 | A1 | 1/2021 | Ianchulev | |
| 2021/0177656 | A1 | 6/2021 | Gallardo et al. | |
| 2021/0212859 | A1 | 7/2021 | Koontz et al. | |
| 2021/0275353 | A1 | 9/2021 | Ichikawa et al. | |
| 2021/0290435 | A1 | 9/2021 | Ianchulev | |
| 2021/0330498 | A1 | 10/2021 | Gooi et al. | |
| 2021/0353463 | A1 | 11/2021 | Kahook et al. | |
| 2021/0386584 | A1 | 12/2021 | Badawi et al. | |
| 2022/0233353 | A1* | 7/2022 | Carter | A61M 1/80 |
| 2022/0323254 | A1 | 10/2022 | Clauson et al. | |
| 2023/0165715 | A1 | 6/2023 | Schuster et al. | |

FOREIGN PATENT DOCUMENTS

| | | | |
|---|---|---|---|
| EP | 2303203 | B1 | 6/2012 |
| EP | 2754427 | B1 | 4/2019 |
| EP | 2844200 | B1 | 11/2020 |
| EP | 3755288 | A1 | 12/2020 |
| EP | 3277236 | B1 | 6/2021 |
| EP | 3870121 | A1 | 9/2021 |
| EP | 3875066 | A1 | 9/2021 |
| GB | 1349881 | A | 4/1974 |
| WO | WO-01/021058 | A2 | 3/2001 |
| WO | WO-2012/162493 | A2 | 11/2012 |
| WO | WO-2013/141898 | A1 | 9/2013 |
| WO | WO-2013/163034 | A1 | 10/2013 |
| WO | WO-2014/187435 | A1 | 11/2014 |
| WO | WO-2018/151808 | A1 | 8/2018 |
| WO | WO-2021/113399 | A1 | 6/2021 |
| WO | WO-2021/127205 | A1 | 6/2021 |
| WO | PCT/US2022/24108 | | 4/2022 |
| WO | PCT/US2022/51420 | | 11/2022 |
| WO | PCT/US2023/60550 | | 1/2023 |

* cited by examiner

MECHANICAL HOLE PUNCH FOR THE REDUCTION OF INTRAOCULAR PRESSURE AND METHODS OF USE

CROSS-REFERENCE TO RELATED APPLICATIONS

This application claims the benefit of priority under 35 U.S.C. § 119 (c) to U.S. Provisional Patent Application Ser. No. 63/266,720, filed Jan. 12, 2022. The disclosure of the application is incorporated by reference in its entirety.

BACKGROUND

Glaucoma is a complicated disease in which damage to the optic nerve leads to progressive vision loss and is the leading cause of irreversible blindness. Aqueous humor is the fluid that fills the anterior chamber in front of the iris and the posterior chamber of the eye behind the iris. Vitreous humor or vitreous body is a gel-like material found in the posterior segment of the eye posterior of the capsular bag. FIG. 1 is a diagram of the front portion of an eye 5 showing the lens 7, cornea 8, iris 9, ciliary body 6 including ciliary processes 4, trabecular meshwork 10, and Schlemm's canal 12. The aqueous humor is a fluid produced by the ciliary body 6 that lies behind the iris 9 adjacent to the lens 7. This aqueous humor washes over the lens 7 and iris 9 and flows to the drainage system located in the angle of the anterior chamber. The angle of the anterior chamber, which extends circumferentially around the eye, contains structures that allow the aqueous humor to drain.

Some of the aqueous humor is absorbed through the trabecular meshwork 10 into Schlemm's canal 12 into collector channels and passing through the sclera 15 into the episcleral venous circulation. The trabecular meshwork 10 extends circumferentially around the anterior chamber 16 in the angle. The trabecular meshwork 10 limits the outflow of aqueous humor. Schlemm's canal 12 is located beyond the trabecular meshwork 10. The two arrows in the anterior chamber 16 of FIG. 1 show the flow of aqueous humor from the ciliary body 6, over the lens 7, over the iris 9, through the trabecular meshwork 10, and into Schlemm's canal 12 and its collector channels.

In some cases glaucoma is caused by blockage of aqueous humor outflow such as by sclerosis of the trabecular meshwork, pigment or membrane in the angle. In other cases, blockage is due to a closure of the angle between the iris and the cornea. This angle type of glaucoma is referred to as "angle-closure glaucoma". In the majority of glaucoma cases, however, called "open angle glaucoma", the cause is unknown.

Treatments of glaucoma attempt to lower intraocular pressure (IOP) pharmacologically or by surgical intervention that enhance outflow of aqueous humor through the outflow pathways. Ab externo trabeculectomy is a type of glaucoma surgery that creates a new path as a "controlled" leak for fluid inside the eye to drain out. Conventionally, a partial thickness scleral flap is formed followed by the creation of a small hole into the anterior chamber. Aqueous humor can flow into the subconjunctival space creating a filtering bleb. The scleral flap is raised up and a blade used to enter the anterior chamber. During the operation a hole is created under the scleral flap that is fluidically connected to the anterior chamber creating an opening. The opening is partially covered with the scleral flap. A small conjunctival "bleb" or bubble appears over the scleral flap, often near the junction of the cornea and the sclera (limbus).

Minimally-invasive surgical procedures provide IOP lowering by enhancing the natural drainage pathways of the eye with minimal tissue disruption. Minimally-invasive glaucoma surgery (MIGS) uses microscopic-sized equipment and tiny incisions. MIGS offers an alternative to conventional glaucoma surgeries with the potential benefit of reducing a patient's dependence on topical glaucoma medication. Trabeculectomies and trabeculotomies can each be performed ab interno, or from inside the anterior chamber. Ab interno approaches aim to decrease IOP by increasing aqueous humor outflow through a direct opening in the trabecular meshwork from within the anterior chamber so that there is direct communication between the anterior chamber and the outer wall of Schlemm's canal. Ab interno approaches include the TRABECTOME (MST/NeoMedix Corp.) electrosurgical instrument that ablates and removes trabecular meshwork, the Kahook Dual Blade (New World Medical) for excisional goniotomy removing a strip of trabecular meshwork, gonioscopy assisted transluminal trabeculotomy (GATT) involving cutting through the trabecular meshwork, cannulating Schlemm's canal, and Omni (Sight Sciences) for performing viscoplasty or trabeculotomy through an ab interno approach for cannulating Schlemm's canal. Other ab interno methods include the iStent (Glaukos) to create pathway through the trabecular meshwork for improved outflow of aqueous humor through Schlemm's canal.

In view of the foregoing, there is a need for improved devices and methods related to ophthalmic surgery for the treatment of glaucoma.

SUMMARY

In an aspect, described is a device to treat an ocular condition including an outer housing having a proximal end region and a distal end region; a rotary housing located within the outer housing rotationally fixed to a rotary spindle and rotationally movable relative to the outer housing; an elongate shaft projecting distally from the distal end region of the outer housing along a central longitudinal axis, at least a distal end region of the elongate shaft being sized for insertion into an eye. The elongate shaft includes an outer shaft having a lumen; and an inner cutting tube positioned at least partially within the lumen of the outer shaft and movable relative to the outer shaft. A distal end of the inner cutting tube has a distal opening defined by a distal cutting surface. A proximal end region of the inner cutting tube is fixedly coupled to the rotary spindle. Upon actuation of the device, the rotary housing rotates causing the rotary spindle and the inner cutting tube to rotate around the central longitudinal axis while simultaneously causing axial extension of the inner cutting tube distally along the central longitudinal axis to advance the distal cutting surface through a target tissue forming a tissue slug.

The device can further include a distal probe having a proximal shaft extending within the inner cutting tube and a barb positioned on a distal end of the proximal shaft. The distal cutting surface can advance beyond the barb of the distal probe upon actuation of the device. The distal probe can be stationary or movable relative to the outer housing. The proximal shaft can have a length to position the barb distal to the distal end of the inner cutting tube so the barb penetrates the target tissue prior to penetration of the tissue by the inner cutting tube. The barb can be sized to be received within a lumen of the inner cutting tube. The barb can be shaped to penetrate and capture the tissue slug. The barb can have an arrowhead shape with one or more bladed wings designed to cut and penetrate tissue in a first direction and snag on the tissue in a second, opposite direction.

The distal cutting surface can be serrated or beveled. The distal cutting surface can have an external bevel, an internal bevel, or both. The distal opening of the inner cutting tube can surround the central longitudinal axis. The elongate shaft can include a curve or a bend and the distal opening of the inner cutting tube is not coaxial with the central longitudinal axis. The outer shaft can be integral with the outer housing or can be adjustably attached to the outer housing.

The rotary motion of the rotary housing can be achieved mechanically via a torsion spring. The torsion spring can encircle a portion of the rotary housing and can be configured to place the rotary housing under a torsional load. The device can further include an actuator configured to initiate motion of the inner cutting tube. The actuator can transform potential energy of the torsion spring into rotational and axial motion of the inner cutting tube. The actuator can be configured to engage at least a portion of the rotary housing. Actuating the actuator can release engagement between the actuator and the rotary housing allowing free rotation of the rotary housing relative to the outer housing due to the torsional load applied by the torsion spring. The rotary housing can incorporate a thread on an external surface of the rotary housing that is configured to engage a corresponding thread on an inner surface of the outer housing. Rotation of the rotary housing can translate into axial motion of the rotary housing due to engagement between the thread on the external surface and the corresponding thread on the inner surface. The torsion spring can cause rotation of the rotary housing around the central longitudinal axis and axial motion of the rotary housing along the central longitudinal axis.

The device can further include a vacuum source configured to apply a vacuum through the inner cutting tube. The vacuum source can be an external vacuum source or an internal vacuum source located within the outer housing. The internal vacuum source can be a syringe mechanism comprising the rotary housing and the rotary spindle. Axial motion of the rotary housing in a proximal direction relative to the rotary spindle can create the vacuum within the outer housing. The vacuum generated by the internal vacuum source can be exposed to the inner cutting tube upon actuation of inner cutting tube motion. The vacuum can be sufficient to draw the target tissue toward the distal end of the inner cutting tube during cutting the target tissue and without drawing the target tissue into the distal opening. The vacuum can be sufficient to draw the tissue slug through at least a portion of the inner cutting tube.

The inner cutting tube can be configured to move axially by at least 50 microns up to about 350 microns. The rotary spindle can be axially movable relative to the rotary housing and axially movable relative to the outer housing along the central longitudinal axis. A spring located within the outer housing can be arranged to urge the rotary spindle in a distal direction within the outer housing. The rotary spindle can include a plurality of ridges on a distal-facing surface configured to mate with a corresponding plurality of ridges within the outer housing urging the rotary spindle in a proximal direction and compressing the spring located within the outer housing. Interdigitation of the plurality of ridges on the distal-facing surface with the corresponding plurality of ridges within the outer housing can cause distal extension of the inner cutting tube as the spring urges the rotary spindle in a distal direction relative to the outer housing.

The outer shaft can be configured to prevent insertion of the inner cutting tube through the target tissue beyond a maximum depth. A luer connection can be incorporated that is configured to receive tubing for supply of irrigation fluid to the eye through the elongate shaft during use of the device. Irrigation fluid can be deliverable to the eye through an annular space between an external surface of the inner cutting tube and an internal surface of the outer tube.

The device can further include one or more light sources. The one or more light sources can be configured for visualization, targeting, and/or photobiomodulation through the elongate shaft. At least one of the one or more light sources can include a laser light source configured to ablate tissue. The laser light source can be configured to ablate the tissue slug within the inner cutting tube. The device can further include one or more lenses for the purpose of visualization during a procedure using the device.

In an interrelated implementation, provided is a method of using a device to treat an ocular condition including inserting a distal end of an elongate shaft of the device into a patient's eye and advancing the distal end towards target tissue; simultaneously applying a rotational force and a linear force against the target tissue with the distal end of the elongate shaft; perforating the target tissue with the distal end forming a tissue slug; and capturing the tissue slug for removal from the eye. The target tissue can include a trabecular meshwork tissue. The method can further include generating a vacuum within a lumen of the elongate shaft, the vacuum being generated upon the applying of the rotational force.

In an interrelated implementation, provided is a device to treat an ocular condition including an outer housing having a proximal end region and a distal end region; a rotary housing located within the outer housing rotationally fixed to a rotary spindle and rotationally movable relative to the outer housing; an elongate shaft projecting distally from the distal end region of the outer housing along a central longitudinal axis, at least a distal end region of the elongate shaft being sized for insertion into an eye. The elongate shaft includes an outer shaft having a lumen; and an inner cutting tube positioned at least partially within the lumen of the outer shaft and movable relative to the outer shaft. A distal end of the inner cutting tube includes a distal opening defined by a distal cutting surface. A proximal end region of the inner cutting tube is fixedly coupled to the rotary spindle. Rotation of the rotary housing causes the inner cutting tube to rotate around the central longitudinal axis thereby generating a vacuum within a lumen of the inner cutting tube and simultaneously causing axial extension of the inner cutting tube distally along the central longitudinal axis.

In an interrelated implementation, provided is a device to treat an ocular condition including an outer housing having a proximal end region and a distal end region; a rotary housing located within the outer housing rotationally fixed to a rotary spindle and rotationally movable relative to the outer housing; an elongate shaft projecting distally from the distal end region of the outer housing along a central longitudinal axis, at least a distal end region of the elongate shaft being sized for insertion into an eye. The elongate shaft includes an outer shaft having a lumen; and an inner cutting tube positioned at least partially within the lumen of the outer shaft and movable relative to the outer shaft. A distal end of the inner cutting tube has a distal opening defined by a distal cutting surface. A proximal end region of the inner cutting tube is fixedly coupled to the rotary spindle. Rotation of the rotary housing causes the inner cutting tube to rotate around the central longitudinal axis thereby exposing a lumen of the inner cutting tube to a vacuum and simultaneously causing axial extension of the inner cutting tube distally along the central longitudinal axis.

In some variations, one or more of the following can optionally be included in any feasible combination in the above methods, apparatus, devices, and systems. More details are set forth in the accompanying drawings and the description below. Other features and advantages will be apparent from the description and drawings.

BRIEF DESCRIPTION OF THE DRAWINGS

These and other aspects will now be described in detail with reference to the following drawings. Generally, the figures are not to scale in absolute terms or comparatively, but are intended to be illustrative. Also, relative placement of features and elements may be modified for the purpose of illustrative clarity.

It should be appreciated that the drawings are for example only and are not meant to be to scale. It is to be understood that devices described herein may include features not necessarily depicted in each figure.

DETAILED DESCRIPTION

Disclosed is a fully hand-held device for increasing aqueous humor outflow for the purpose of controlling intraocular pressure (IOP). More particularly and as will be described in detail below, the devices described herein involve mechanically creating a hole using a rotating biopsy punch to enhance part of the natural drainage pathways of the eye by trephining one or more tissue slugs from the trabecular meshwork.

Figure 1:
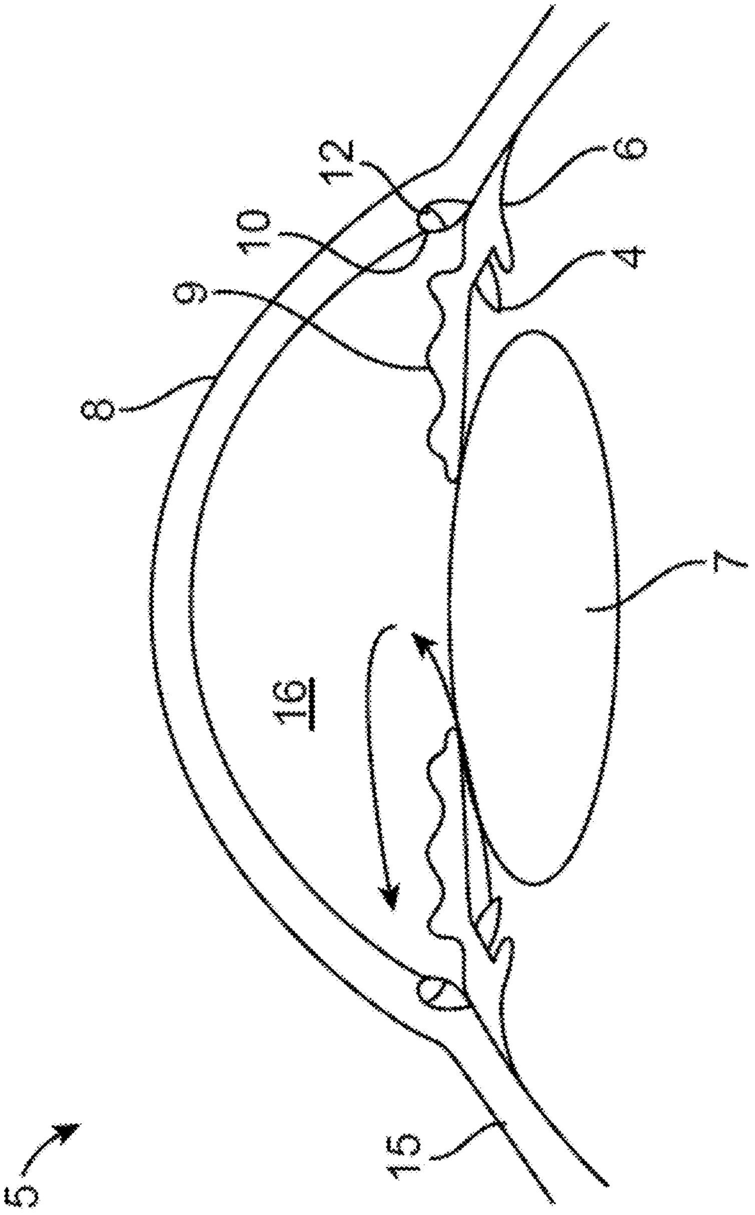
FIG. 1 is a diagram of the front portion of the eye.
Figure 2A:
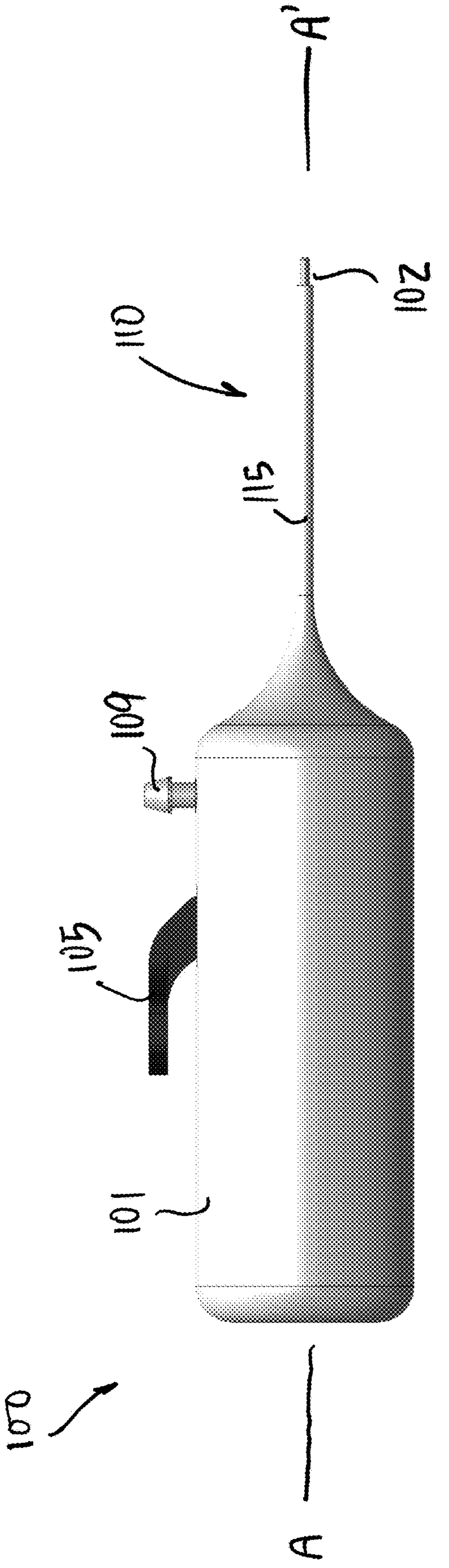
FIG. 2A is a side view schematic illustrating an implementation of a trephining device.
Figure 2B:
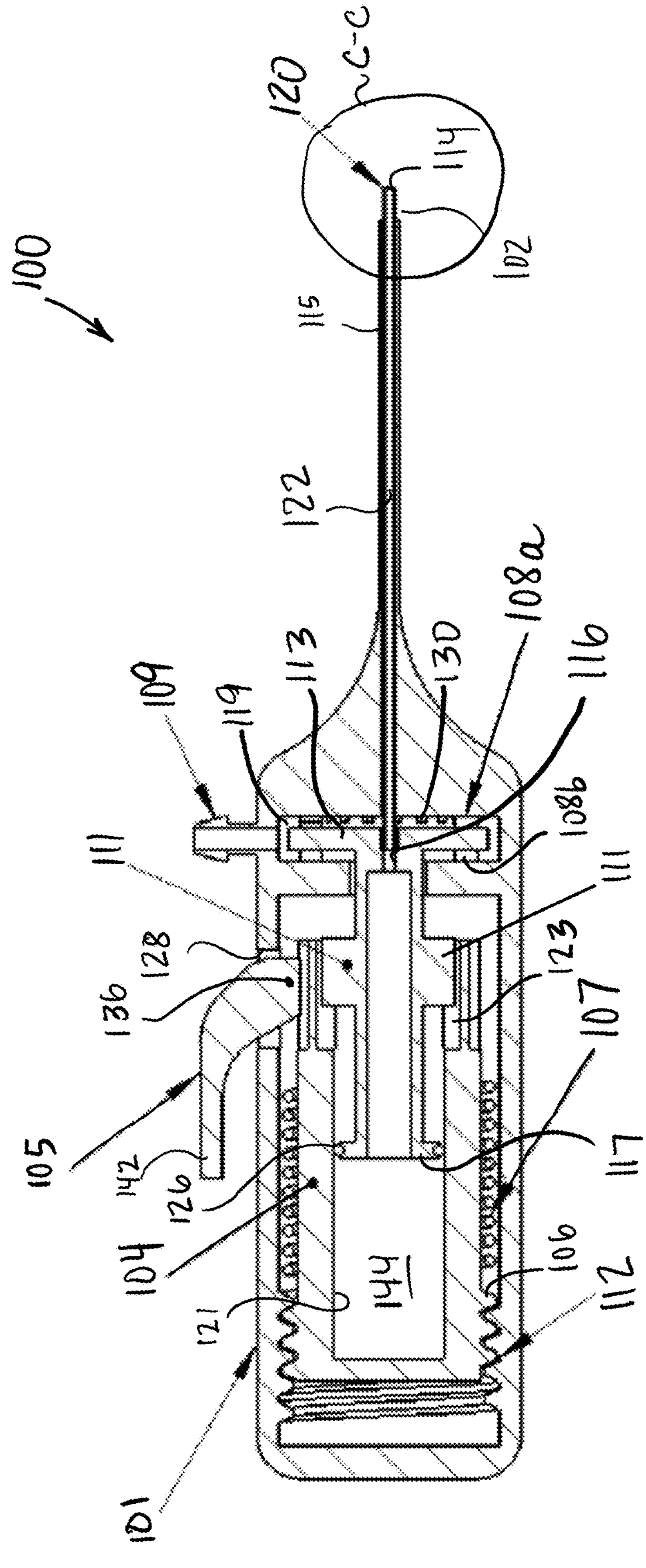
FIG. 2B is a cross-sectional view of the device of FIG. 2A.
Figure 2C:
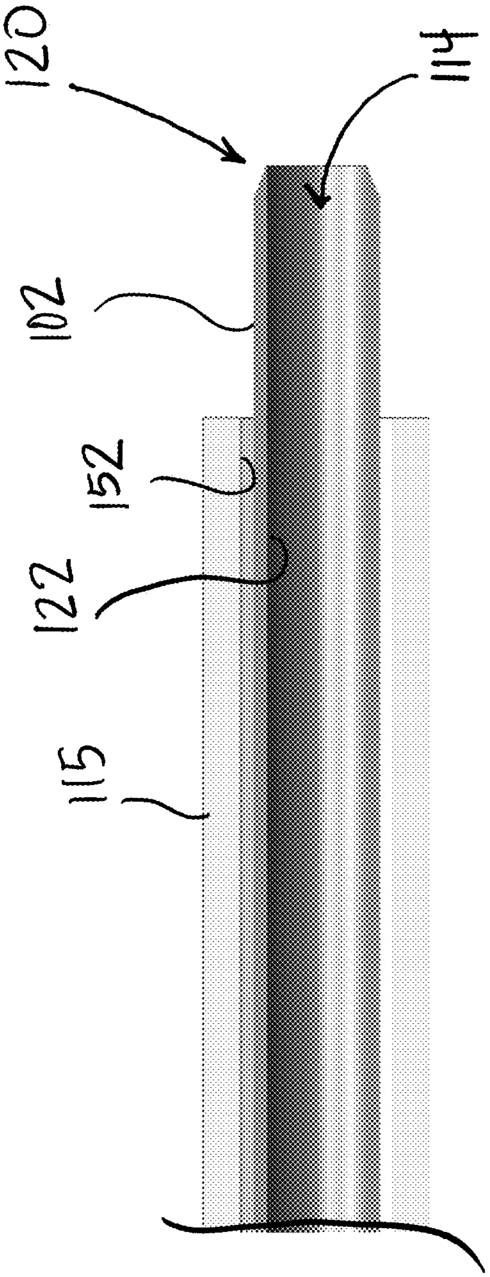
FIG. 2C is a detailed view of the device of FIG. 2B taken at circle C-C.

FIGS. 2A-2C and also FIGS. 5A-5C, 6A-6D are schematics illustrating implementations of trephining devices 100. The device 100 can include a handle or outer housing 101 having a proximal end region and a distal end region. The proximal end region is configured to be held by a user during use whereas the distal end region is configured to insert at least partially within the eye. An elongate shaft 110 projects distally from a region of the outer housing 101. At least the distal end of the elongate shaft 110 is sized to be inserted into the anterior chamber 16 of the eye such as through a corneal incision. The elongate shaft 110 can include an inner cutting tube 102 having a lumen 122, the inner cutting tube 102 extending through and movable relative to a lumen of an outer shaft 115. The outer shaft 115 can be integral with the outer housing 101. The inner cutting tube 102 can be advanced relative to the distal end of the outer shaft 115 so as to contact and penetrate intraocular tissue such as the trabecular meshwork for the purpose of cutting the tissue. The inner cutting tube 102 can penetrate and enter Schlemm's canal whereas the outer shaft 115 is sized and designed to remain outside the trabecular meshwork and the canal. The inner cutting tube 102 is movable relative to the housing 101 in order to trephine tissue. Upon actuation of the device 100, the inner cutting tube 102 rotates around the longitudinal axis A while simultaneously extending distally along the longitudinal axis A to cut through the tissue, which is described in more detail below.

The elongate shaft 110 can have a central longitudinal axis A' that is coaxial with a longitudinal axis A of the housing 101. The distal cutting surface at the distal end 120 of the inner cutting tube 102 forms an opening that surrounds the longitudinal axis A so that the axis A extends through a center of the tube 102. In other implementations, the elongate shaft 110 has a curve or a bend near its distal end so that the distal opening 114 at the distal end 120 of the cutting tube 102 is off-set from the longitudinal axis A of the shaft 110. The inner cutting tube 102 can be circular in cross-section or some other geometry including oval, lenticular, square, rectangular, diamond, or other shape. The distal end 120 of the inner cutting tube 102 can be serrated or have a serrated edge similar to a saw blade to trephine the tissue. The distal end 120 edge can also be beveled to form a trephine. FIG. 2C is a detail view of the distal end 120 of the inner cutting tube 102 taken at circle C-C in FIG. 2B showing a bevel. The distal end 120 of the inner cutting tube 102 can be ground to include an external and/or an internal bevel so as to form a single or double bevel cutting edge. The distal end 120 of the cutting tube 102 can also be a neutral bevel.

The inner cutting tube 102 can be in a range of about 0.006" outer diameter to about 0.05" outer diameter. The inner cutting tube 102 can be sized to create an opening in the tissue that is in a range of about 100 microns to about 400 microns in diameter. The tissue slug created by the distal end 120 of the cutting tube 102 is sized to be removed through the lumen 122 of the cutting tube 102.

Figure 3:
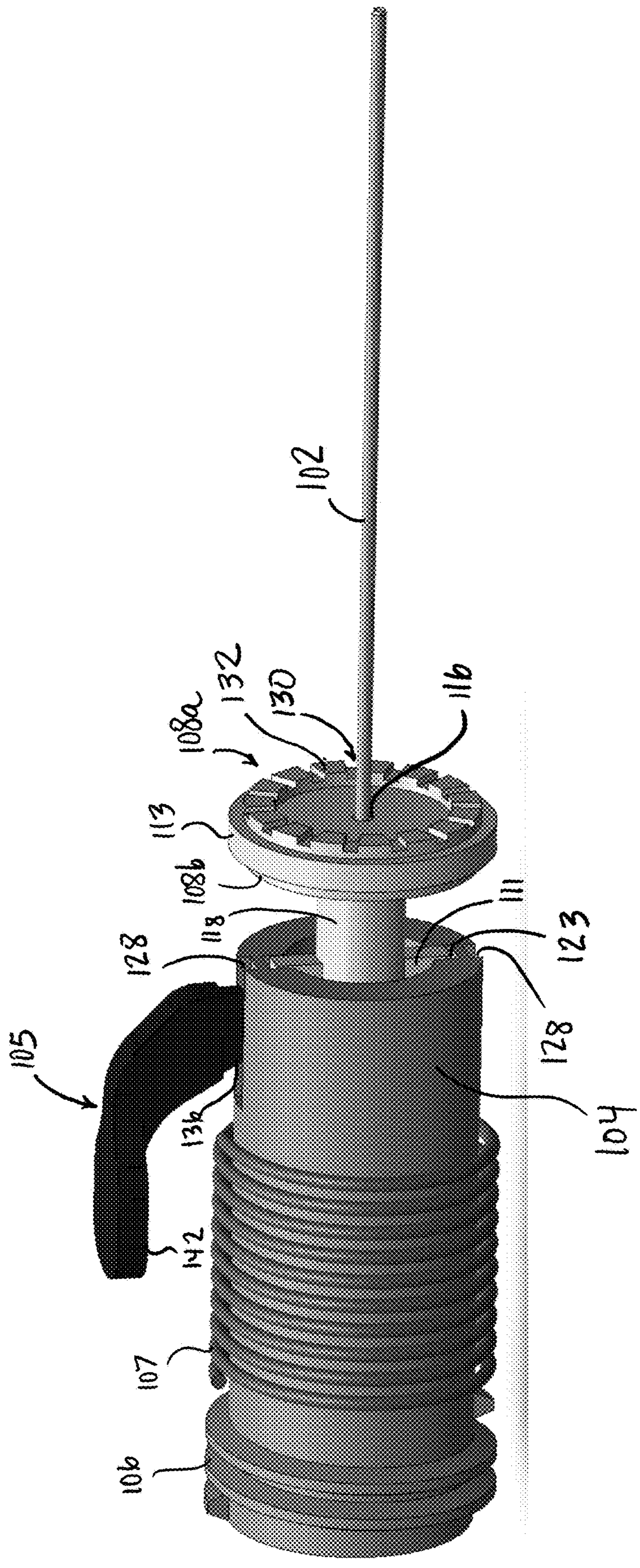
FIG. 3 is a perspective view of the device of FIG. 2A with the outer housing removed.
Figure 4:
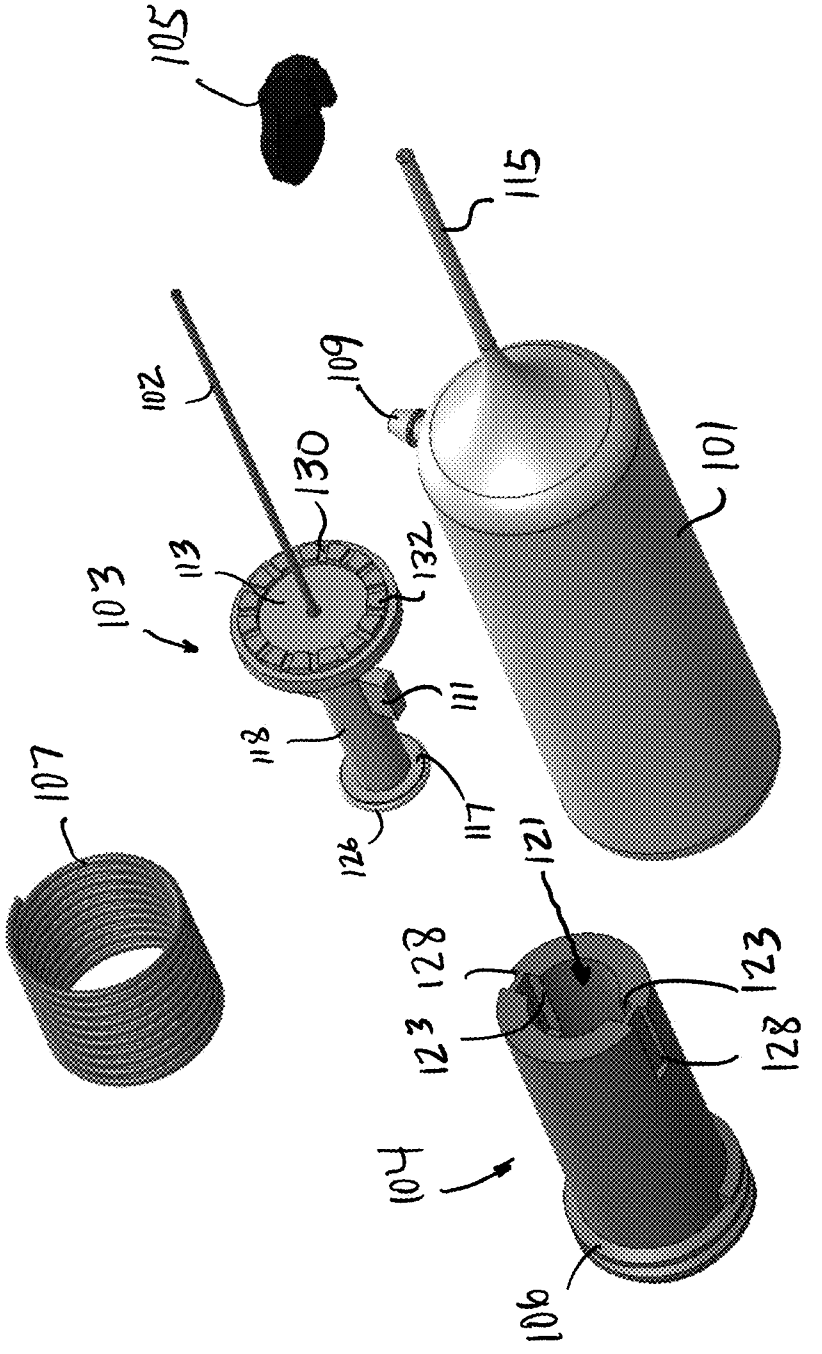
FIG. 4 is a partially exploded view of the device of FIG. 3.

The proximal end region of the inner cutting tube 102 is rigidly coupled to a rotary spindle 103 positioned within the housing 101 (see FIGS. 2B, 3, and also FIGS. 5A-5C, and FIGS. 6A-6D). FIG. 3 is a perspective view of the device 100 with the outer housing 101 removed. FIG. 4 is a partially exploded view of the device 100. The rotary spindle 103 can include a distal plate 113 having a central opening 116 configured to receive the proximal end region of the inner cutting tube 102. The rotary spindle 103 also can include a proximal plate 117 positioned at a proximal end region of the rotary spindle 103 opposite and separated from the distal plate 113 by a central shaft 118. A distal thrust bearing 108*a* lies against a distal-facing surface of the perimeter region of the distal plate 113. A proximal thrust bearing 108*b* lies against a proximal-facing surface of the perimeter region of the distal plate 113. The proximal plate 117 of the rotary spindle 103 extends within a bore 121 of a rotary housing 104. An O-ring 126 encircles the proximal plate 117 and seals with the bore 121 of rotary housing 104. The central shaft 118 of the rotary spindle 103 also extends within the bore 121 of the rotary housing 104. The central shaft 118 can include a pair of splines 111 projecting outward from the external surface of the central shaft 118 so as to engage with a pair of slots 123 on an internal surface of the bore 121 of the rotary housing 104. The pair of slots 123 are sized to receive the pair of splines 111. The coupling between the rotary spindle 103 and the rotary housing 104 allows for relative axial motion between them. The slots 123 are sized longer than the splines 111 so that the housing 104 can move relative to the spindle 103 and the splines 111 slide within the slots 123 along longitudinal axis A.

Figure 5A:
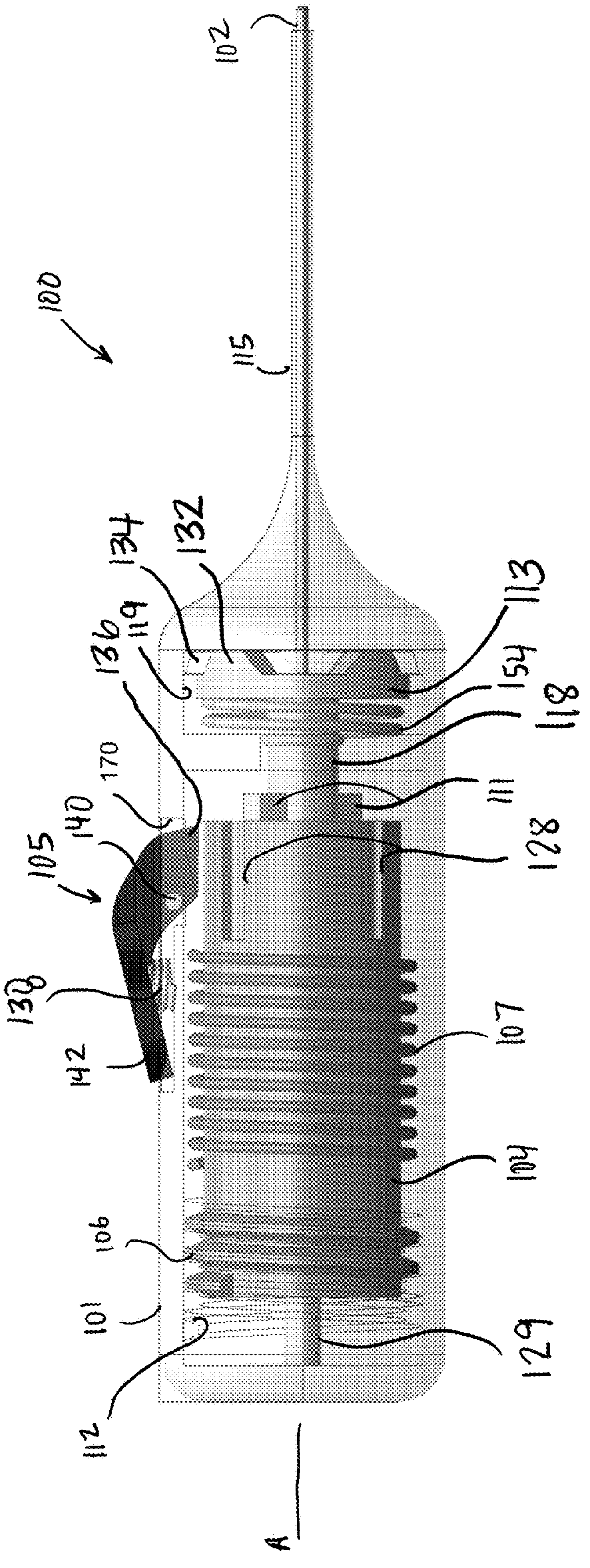
FIG. 5A is a side view illustrating an implementation of a trephining device with the outer housing shown as transparent.
Figure 5B:
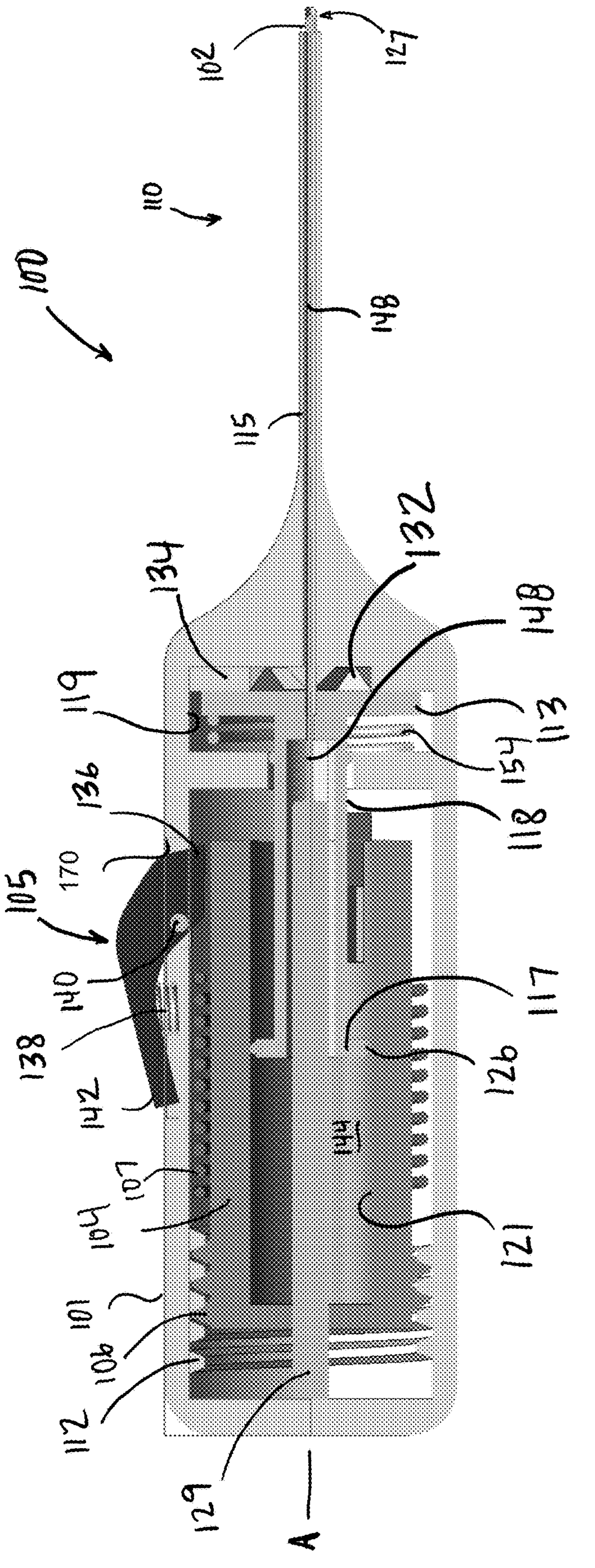
FIG. 5B is a cross-sectional view of the device of FIG. 5A.
Figure 5C:
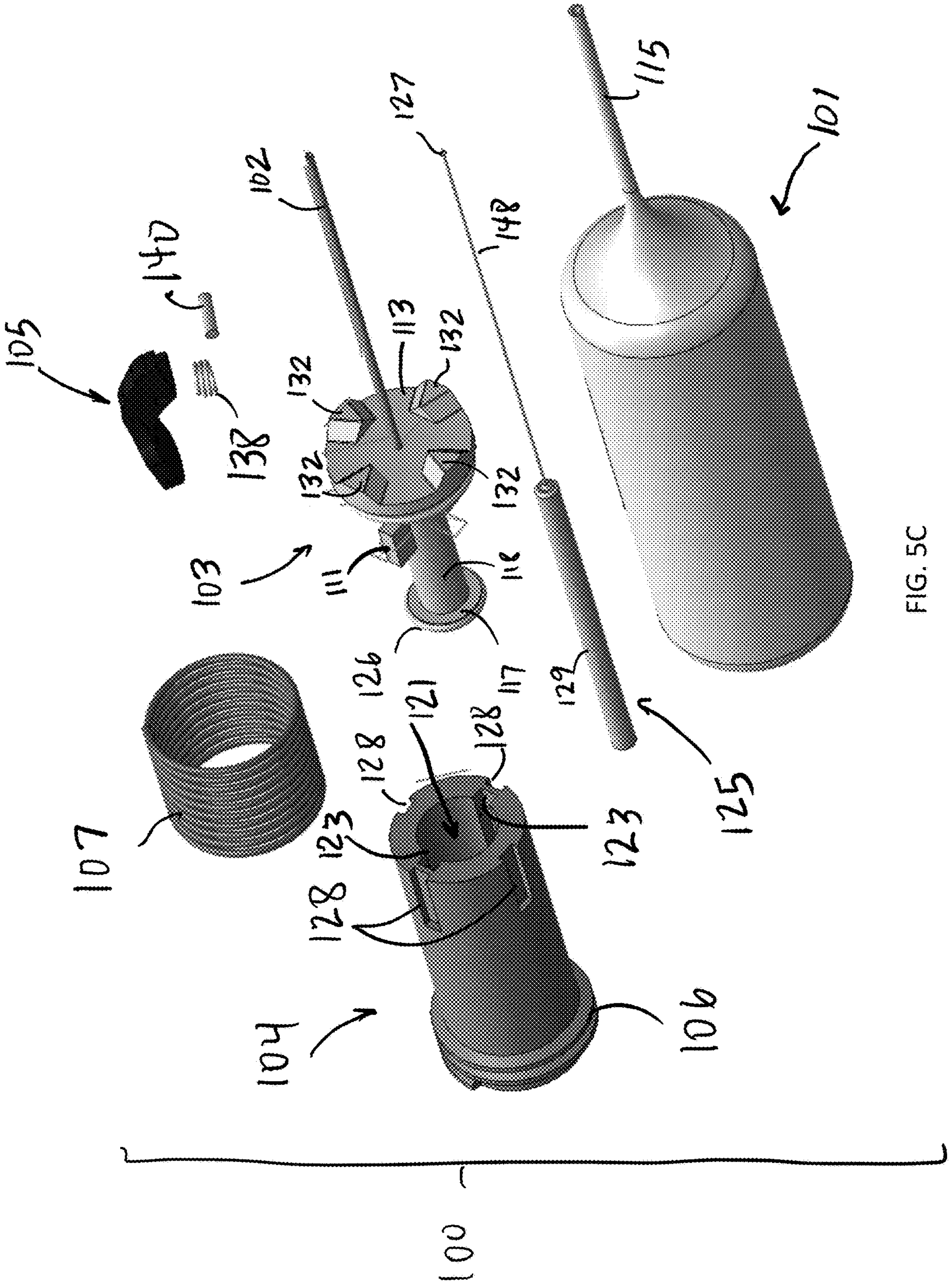
FIG. 5C is a partially exploded view of the device of FIG. 5A.
Figure 6A:
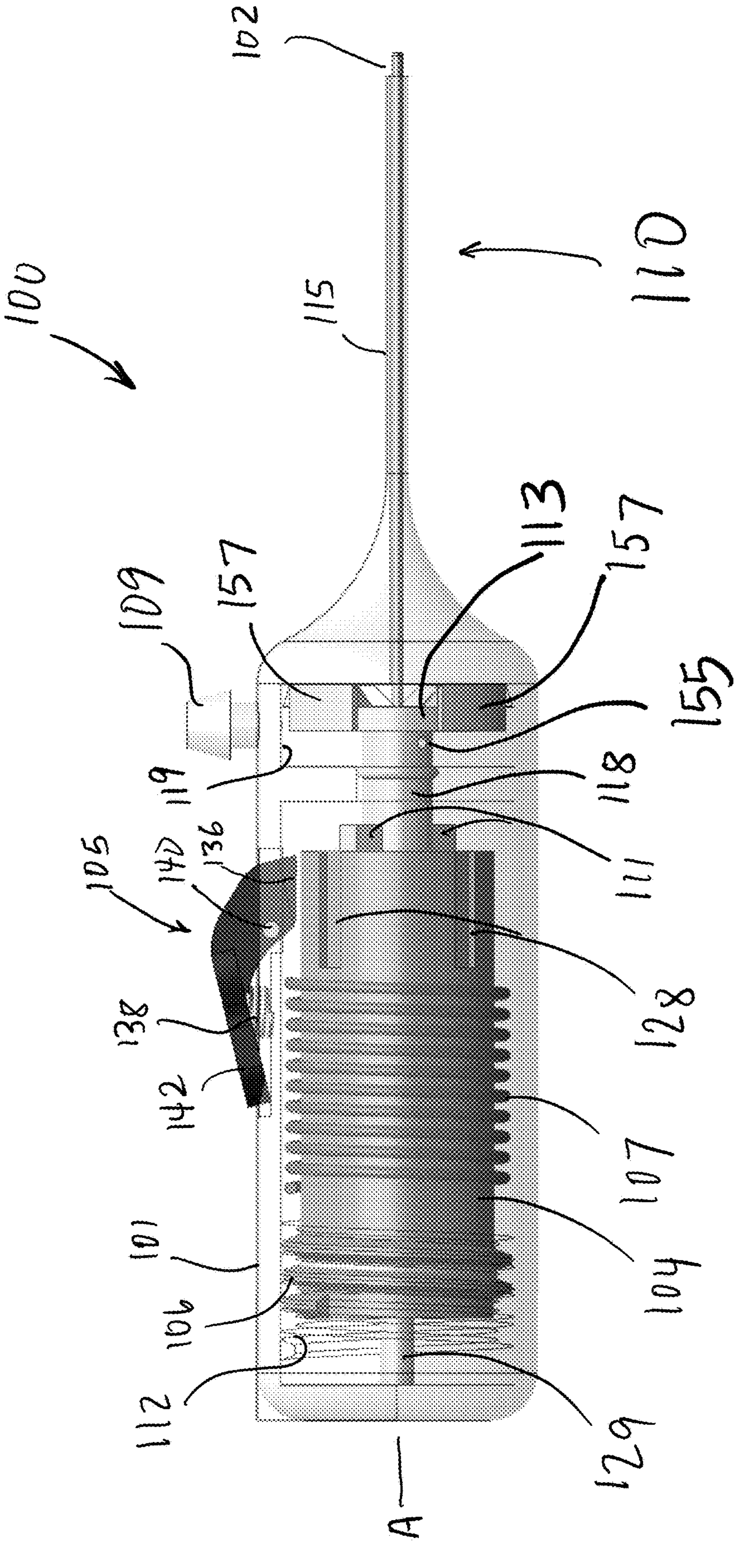
FIG. 6A is a side view illustrating an implementation of a trephining device with the outer housing shown as transparent.
Figure 6B:
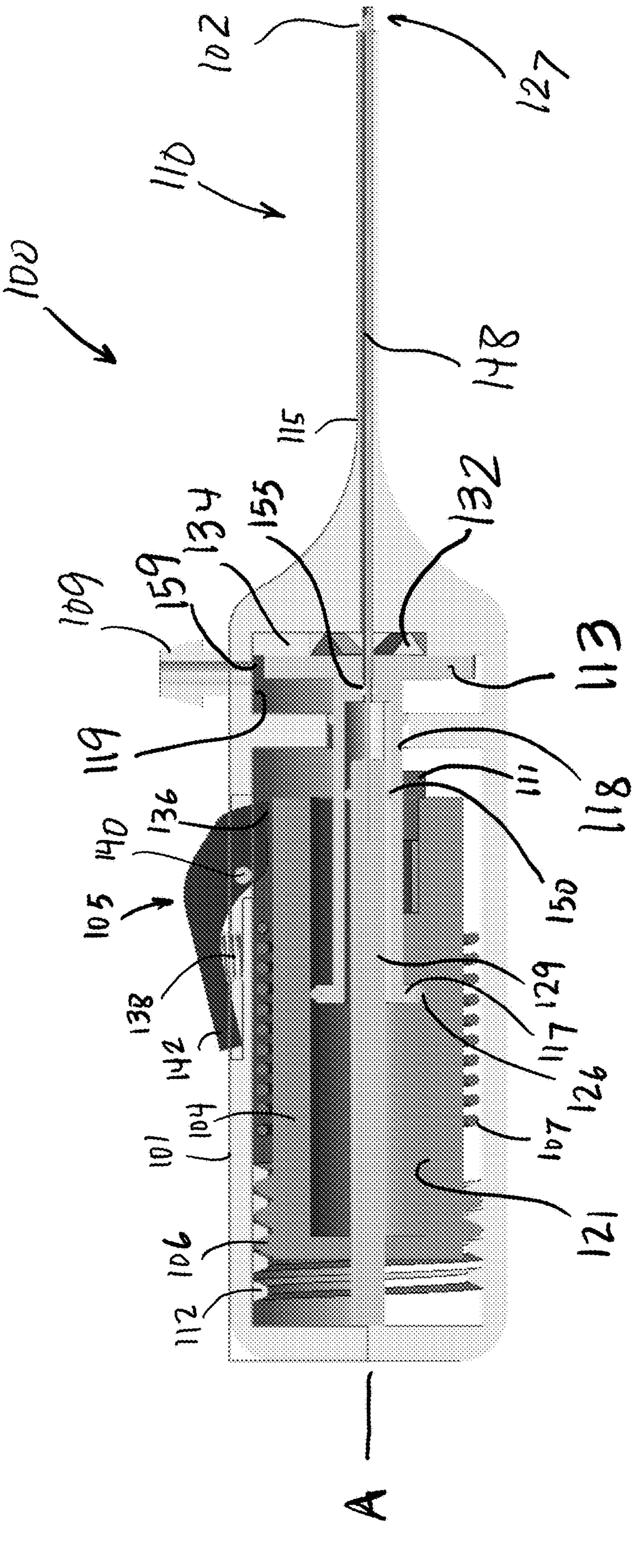
FIG. 6B is a cross-sectional view of the device of FIG. 6A.
Figure 6C:
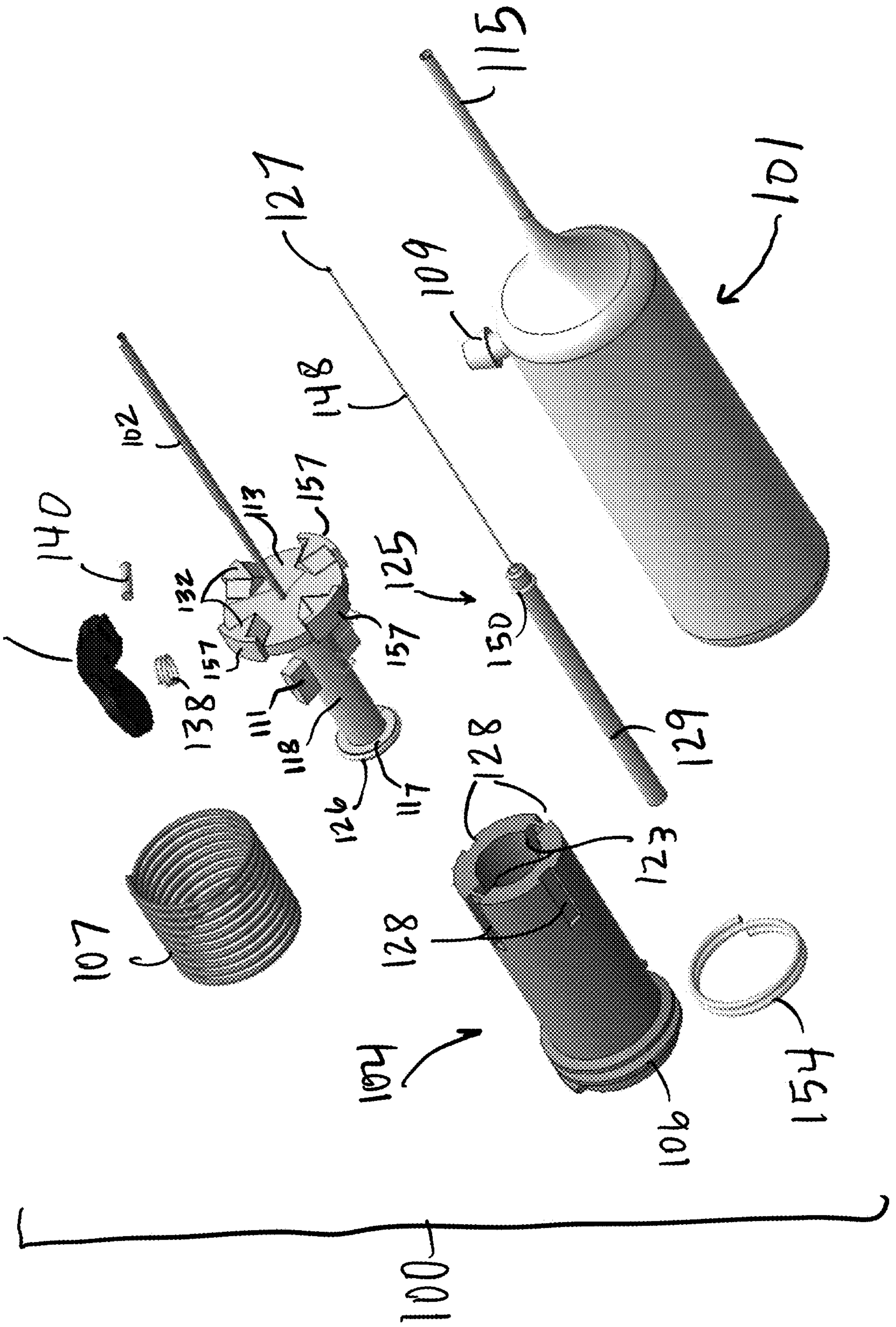
FIG. 6C is a partially exploded view of the device of FIG. 6A.

The distal plate 113 of the rotary spindle 103 is sized to be received within a chamber 119 in the distal end region of the housing 101 (see FIG. 2B and also FIGS. 5A-5B, and FIGS. 6A-6B). The rotary spindle 103 can be spring-loaded to be biased forwards within the chamber 119 by a spring 154 located within the chamber 119 in contact with the proximal-facing surface of the distal plate 113. The spring 154 urges the distal plate 113 towards a distal end of the chamber 119 in the outer housing 101. The distal-facing surface of the distal plate 113 (or the distal thrust bearing 108*a* on the distal-facing surface) incorporates a surface geometry that corresponds to a surface geometry of the chamber 119. For example, the distal-facing surface can incorporate a plurality of ridges 132 that are sized and shaped similarly to a plurality of ridges 134 within the chamber 119. At rest, the ridges 132 on the distal plate 113 are in contact with the ridges 134 of the chamber 119, which urges the spindle 103 in a rearward position keeping the inner cutting tube 102 retracted and the spring 154 compressed. When actuated, the spindle 103 rotates around the central longitudinal axis A. The ridges 132 on the distal plate 113 of the spindle 103 disengage from or slide past the ridges 134 of the chamber 119 so that the ridges 132, 134 interdigitate with one another resulting in the distal plate 113 being urged distally by the spring 154 as the ridges 132 of the distal plate 113 are received within corresponding valleys between ridges 134 of the chamber 119. The inner cutting tube 102 moves distally because it is rigidly fixed to the spindle 103. FIG. 3 shows the plurality of ridges 132 on the distal-facing surface having a square geometry. There are about 15 ridges 132 illustrated in this implementation, however, the number of ridges 132, 134 can vary. FIGS. 5C and 6C show the distal-facing surface of other implementations the spindle 103 having just 4 ridges 132. The ridges 132 shown in FIG. 3 have a square edge such that the sides of each ridge 132 are substantially perpendicular to the upper surface of each ridge 132. The ridges 132 in FIGS. 5C and 6C are shaped so that the sides of each ridge 132 are non-perpendicular to the upper surface of each ridge 132. The ridges 132 can be angled such that the base is wider than the upper surface. This non-perpendicular pyramidal geometry assists relative sliding between the ridges 132 of the spindle 103 and the ridges 134 in the chamber 119.

The rotary motion of the rotary housing 104 can be powered by a motor. Preferably, the rotary motion is achieved mechanically by a torsion spring 107 that encircles a portion of the rotary housing 104 placing the rotary housing 104 under a torsional load (see FIG. 2B and also FIGS. 5A-5C and 6A-6C). The device 100 can include at least one actuator 105 configured to initiate the cutting motion of the cutting tube 102. When the actuator 105 is actuated such as by pressing the trigger or button, an engagement feature 136 on a lower surface of the actuator 105 extending through an opening 170 in the outer housing 101 is moved out of engagement with the rotary housing 104 allowing it to rotate freely relative to the housing 101 due to the force of the torsion spring 107. For example, the rotary housing 104 can incorporate one or more external surface features or detents 128 sized to receive the engagement feature 136 of the actuator 105 (see FIGS. 2B, 3, 4, and 5A-5C). Actuation of the trigger 105 withdraws the engagement feature 136 from the detent 128 releasing the housing 104 from engagement with the actuator 105 thereby turning the potential energy of the torsion spring 107 into rotational motion of the rotary housing 104 powered by the load of the spring 107 and, in turn, distal extension of the inner cutting tube 102. The speed of axial extension powered by the torsion spring 107 can be at least about 0.5 meter/second to about 12 meters/second. The rotary spindle 103 is rotationally fixed to the rotary housing 104 so that it rotates with the rotary housing. The inner cutting tube 102 is rotationally fixed to the rotary spindle 103 so that the inner cutting tube 102 rotates with the rotary spindle 103.

The actuator 105 can be bi-stable so that once it is actuated to release the torsion spring 107, it can return to its original position without additional user input and once again limits the rotation angle of the rotary housing 104. Return of the actuator 105 enables the engagement feature 136 to catch within the next detent 128 and avoids complete unwinding of the torsion spring 107 with a single actuation. The actuator 105 can be released by the user to allow the spring 107 to urge it back into its original position or the actuator 105 can incorporate a catch or other feature that even when the user does not release the actuator 105 the engagement feature 136 is allowed to catch within the next detent 128. FIGS. 5A-5C and also FIGS. 6A-6C illustrate the actuator 105 having a spring 138 configured to pivot the actuator 105 around a pivot pin 140 when at rest. When in the resting configuration, a trigger portion 142 of the actuator 105 is urged upward away from the outer housing 101 and the engagement feature 136 of the actuator 105 is moved downward toward the outer housing 101 and into engagement with one of the detent 128 of the rotary housing 104. When in the depressed configuration, the trigger portion 142 of the actuator 105 is urged downward toward the outer housing 101 and the engagement feature 136 is moved upwards away from the outer housing 101 and out of engagement with the detent 128 of the rotary housing 104. The rotary housing 104 is then free to rotate by force of the torsion spring 107. The spring 138 of the actuator 105 returns the actuator 105 into the resting configuration so that the engagement feature 136 moves into engagement with the detent 128 preventing further rotation of the rotary housing 104. Release of the rotary housing 104 from engagement with the engagement feature 136 of the actuator 105 can result in rotation a number of degrees between neighboring detents 128.

Actuation of the actuator 105 can be performed multiple times to achieve multiple punches before the torsion spring 107 needs to be wound again to reset the device 100. In some methods, a surgeon may create at least one and up to about 10-15 punches through the trabecular meshwork around a circumference of an eye. The devices described herein can be configured to allow for the creation of at least 2, at least 3, at least 4, at least 5, at least 6, up to about 12 actuations of the cutting tube 102 before the device needs to be reset. In turn, the rotary housing 104 can have a number of detents 128 around its circumference to achieve the desired degrees of rotation of the inner cutting tube 102 with each actuation so that a single winding of the torsion spring 107 can provide the desired number of punches without needing to be reset. For example, the rotary housing 104 can include at least 1, 2, 3, 4, or more and up to about 12 detents 128 resulting in 360 degree rotation, 180 degree rotation, 120 degree rotation, 90 degree rotation, up to about 30 degrees of rotation, respectively, of the inner cutting tube 120. FIG. 4 illustrates an implementation of a rotary housing 104 having two detents 128 positioned 180 degrees apart from one another around the longitudinal axis A. Upon actuation, the rotary housing 104 in this implementation rotates 180 degrees upon removal of the engagement feature 136 from the first detent 128 and insertion of the engagement feature 136 into the second detent 128. FIGS. 5C and 6C each illustrate implementations of the rotary housing 104 having four detents 128 positioned 90 degrees apart around the longitudinal axis A. Upon actuation, the rotary housing 104 in these implementations rotate 90 degrees upon removal of the engagement feature 136 from the first detent 128 and insertion of the engagement feature 136 into the adjacent detent 128.

The rotary housing 104 can be reset for creation of additional holes in the trabecular meshwork beyond what a single winding of the torsion spring 107 allows. For example, the rotary housing 104 can include a feature that allows for a user to rotate the rotary housing 104 in a direction opposite of the direction of rotation caused by the torsion spring 107. The feature can be an actuator configured to turn the rotary housing 104 around the longitudinal axis A to reset the torsion spring 107 for additional use such as a dial, wheel, slider, button, or other actuator that is configured to wind the rotary housing 104 and compress the torsion spring 107. The feature can also be actuated by a separate tool that is configured to be inserted into the proximal end of the device. The tool can have a distal end corresponding in size and shape to the feature in the proximal end of the device 100 so that the tool can rotate the rotary housing 104 and wind the torsion spring 107 to reset the device 100 for additional punches.

The interaction between the tissue and the inner cutting tube 102 can be aided by application of negative pressure through the lumen 122 of the cutting tube 102. In some implementations, the device 100 incorporates an internal vacuum source within the housing 101 configured to apply temporary spike in vacuum through the lumen 122 of the cutting tube 102. The internal vacuum source can be a miniature pump within the housing 101 or a manually-actuated source of negative pressure such as a bellows or a syringe mechanism. As discussed above, rotary motion of the rotary housing 104 can simultaneously cause rotary motion around the central longitudinal axis A of the rotary spindle 103 as well as the inner cutting tube 102 fixed to the spindle 103. Rotary motion of the rotary housing 104 also causes axial motion of the cutting tube 102 along the central longitudinal axis A due to the interdigitation of the ridges 132 on the spindle 103 with the ridges 134 in the chamber 119. Rotary motion of the rotary housing 104 can additionally result in the generation of vacuum within the lumen 122 of the inner cutting tube 102. The vacuum is generated once the cutter is actuated in order to aid in removing tissue pieces through the lumen 122.

Again with regard to FIGS. 5A-5C, the external surface of proximal end region of the rotary housing 104 can incorporate a thread 106. The thread 106 engages with corresponding thread 112 on an internal surface of a corresponding end of the housing 101. As the rotary housing 104 rotates around the central longitudinal axis A under load of the torsion spring 107, engagement between threads 106, 112 causes axial translation of the rotary housing 104 in the proximal direction within housing 101. Proximal axial motion of the rotary housing 104 along the longitudinal axis A relative to spindle 103 creates vacuum through the inner cutting tube 102. As discussed above, the rotary spindle 103 includes a proximal plate 117 that is positioned within the bore 121 of the rotary housing 104. The O-ring 126 encircling the proximal plate 117 seals with the internal surface of the bore 121 creating a vacuum chamber 144 in the region of the bore 121 located proximal to the O-ring 126. Motion of the rotary housing 104 in the proximal direction relative to the axially-fixed rotary spindle 103 enlarges the vacuum chamber 144 between the O-ring 126 and the proximal end of the bore 121 thereby generating a vacuum. Thus, actuation of the trigger 105 releases the rotary housing 104 turning the potential energy of the spring 107 into both rotational and axial motion of the inner cutting tube 102 as well as axial motion of the rotary housing 104 generating vacuum within the vacuum chamber 144 that can be exposed to the inner cutting tube 102. The lumen 122 of the inner cutting tube 102 is arranged to be exposed to the vacuum generated within the vacuum chamber 144.

The vacuum through the inner cutting tube 102 can be used to draw material towards the distal opening 114 at the distal end 120 of the cutting tube 102 during a procedure. The vacuum applied is sufficient to maintain contact between the distal end 120 of the cutting tube 102 and the tissue without drawing the tissue into the distal opening 114 of the cutting tube 102 prior to cutting. The vacuum can also be useful for drawing the tissue slug 18 into the lumen 122 of the cutting tube 102 so as to be removed through the lumen 122.

In other implementations, the device 100 can be connected to an external vacuum source in order to apply external vacuum through the lumen 122 of the cutting tube 102. At rest, the external vacuum can be blocked off from the lumen 122 such as by a valve. When the cutting tube 102 is actuated, the valve can open allowing vacuum to be applied through the lumen 122. When the cutting tube 102 returns to rest, the valve closes.

FIGS. 6A-6D illustrates an implementation for connecting to an external vacuum source through a luer connection 109. Like other implementations of the device 100, rotation of the rotary housing 104 causes the inner cutting tube 102 to rotate around the central longitudinal axis A and simultaneously axially extend distally along the central longitudinal axis A. Additionally, the lumen 122 of the inner cutting tube 102 is exposed to a vacuum generated by an external vacuum source (not shown) connected at the luer connection 109 upon rotation.

Figure 6D:
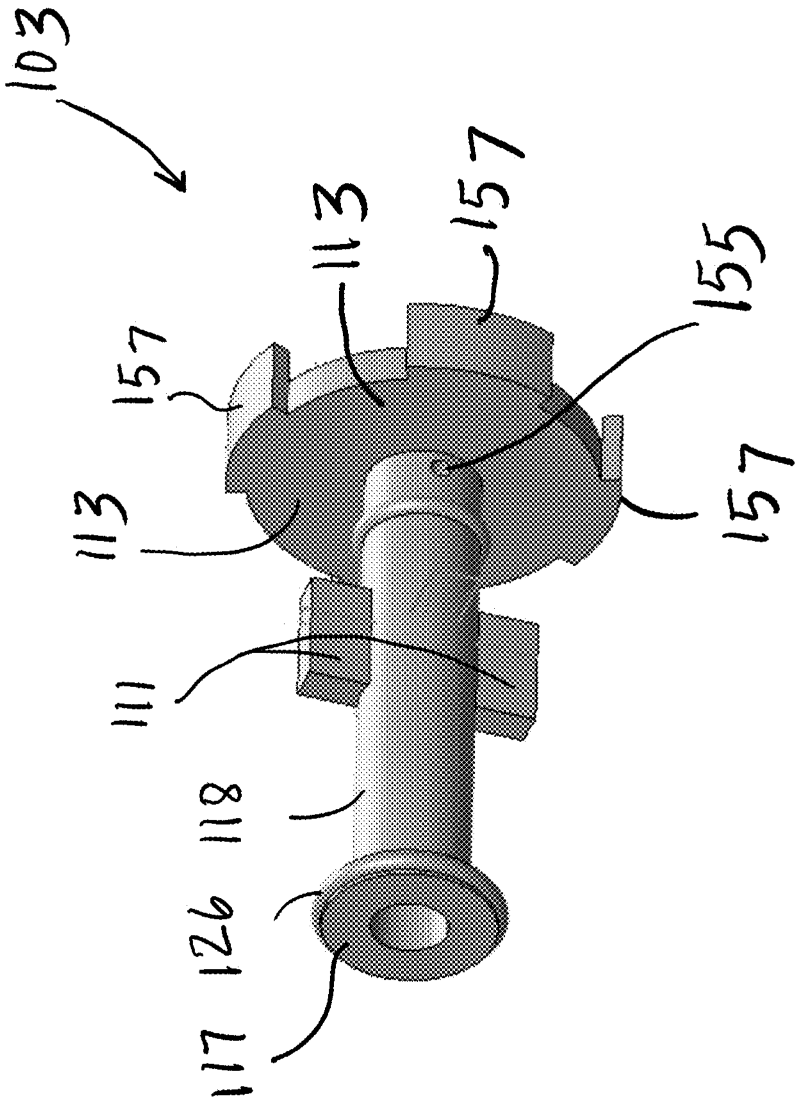
FIG. 6D is a detail view of the rotary spindle of the device of FIG. 6A.

FIG. 6A is a side view illustrating an implementation of a trephining device with the outer housing shown as transparent and FIG. 6B is a cross-sectional view of the device of FIG. 6A. FIG. 6C is a partially exploded view of the device. The rotary spindle 103 is best shown in FIG. 6D. The rotary spindle 103 includes a distal plate 113 having a central opening 116 configured to receive the proximal end region of the inner cutting tube 102. The proximal plate 117 of the rotary spindle 103 is positioned opposite from the distal plate 113 and separated by the central shaft 118. As in other implementations, the distal plate 113 of the rotary spindle 103 is positioned within chamber 119 in the distal end region of the housing 101. The chamber 119 is configured to be placed in fluid communication with the luer 109 connected to an external vacuum source. Rotation of the spindle 103 upon actuation of the device opens the fluid connection between the luer 109 and the chamber 119. The lumen 122 of the inner cutting tube 102 is in fluid communication with the chamber 119 through an opening 155 through the central shaft 118 of the rotary spindle 103. The distal plate 113 of the rotary spindle 103 is best shown in FIGS. 6C-6D. The distal-facing surface of the distal plate 113 incorporates a plurality of ridges 132 that are sized and shaped similarly to a plurality of ridges 134 within the chamber 119. At rest, the ridges 132 on the distal plate 113 are in contact with the ridges 134 of the chamber 119, which urges the spindle 103 in a rearward position keeping the inner cutting tube 102 retracted. Each ridge 132 on the distal plate 113 can include an outer perimeter feature 157 configured to cover and seal the opening 159 between the luer 109 and the chamber 119. This outer perimeter feature 157 by closing the opening 159 prevents the chamber 119 and the lumen 122 of the inner cutting tube 102 from being exposed to the vacuum from the external vacuum source through the luer 109. When actuated, the spindle 103 rotates around the central longitudinal axis A from the first detent 128 to the neighboring detent 128. The ridges 132 on the distal plate 113 of the spindle 103 disengage from or slide past the ridges 134 of the chamber 119 so that the ridges 132, 134 interdigitate with one another resulting in the distal plate 113 being urged distally as the ridges 132 of the distal plate 113 are received within corresponding valleys between the ridges 134 of the chamber 119. Additionally, the outer perimeter feature 157 is moved away from covering the opening 159 between the luer 109 and the chamber 119 causing a vacuum to be generated within the chamber 119. This exposes the lumen 122 of the inner cutting tube 102 to the vacuum in the chamber 119 through the opening 155 in the central shaft 118 of the spindle 103. The proximal shaft 129 of the distal probe 125 can incorporate an O-ring 150 so that the vacuum generated within the chamber 119 is prevented from venting out through the proximal region of the device. In this implementation, chamber 119 forms the vacuum chamber rather than the vacuum chamber being formed within the bore 121 of the rotary housing 104. The outer perimeter feature 157 forms a valve that rotates along with the rotary spindle 103 around the longitudinal axis A thereby alternatingly closing off the lumen 122 from the vacuum when aligned with the opening 159 prior to distal extension of the inner cutting tube 102 and exposing the lumen 122 to the vacuum when moved away from the opening 159 during distal extension of the inner cutting tube 102.

Figure 7:
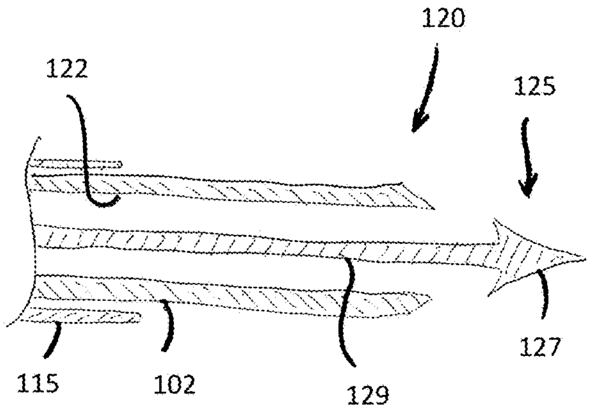
FIG. 7 is a cross-sectional schematic view of a distal end region of the device illustrating mechanical punch of the trabecular meshwork.
Figure 8A:
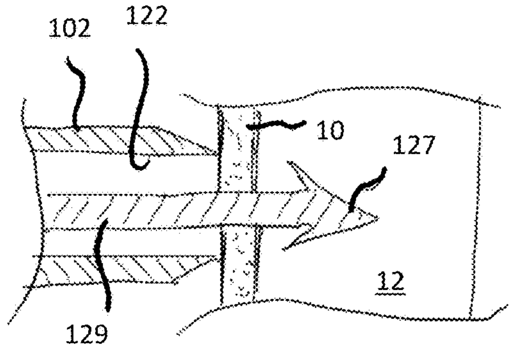
FIGS. 8A-8B are cross-sectional schematic views of the distal end region of the device after penetration of the trabecular meshwork with the probe and after advancement of the cutting tube over the probe, respectively.
Figure 8B:
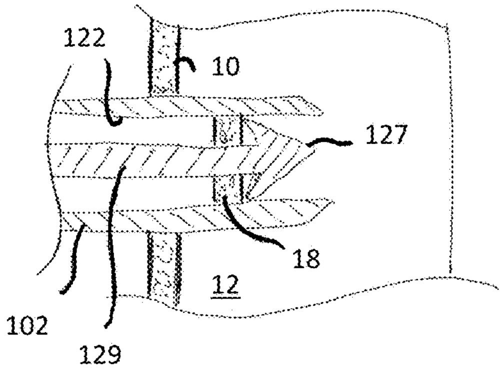

Withdrawal of the tissue slug 18 can be aided by the presence of a probe 125 extending within the lumen 122 of the inner cutting tube 102 (see FIGS. 5A-5C, 6A-6C, and also FIG. 7, and FIGS. 8A-8B). The probe 125 can include a proximal shaft 129 and a distal shaft 148 having a barb 127 positioned on its distal end. The probe 125 can be designed to move distally and/or proximally relative to the inner cutting tube 102, such as with an actuator on the device (e.g., slider, button, trigger, dial or other type of actuator). Preferably, the probe 125 is a stationary, passive feature. For example, the proximal shaft 129 can be affixed to the outer housing 101 at a proximal end region and extend centrally through the bore 121 of the rotary housing 104 and through an internal bore in the central shaft 118 of the rotary spindle 103. The proximal shaft 129 can incorporate an O-ring or other sealing element 150 (see FIG. 6C) that is configured to seal with the internal bore of the central shaft 118. The distal shaft 148 of the probe 125 can extend through the lumen 122 of the inner cutting tube 102 so that the barb 127 positioned on its distal end can penetrate and capture the tissue slug 18. Thus, the proximal shaft 129 and distal shaft 148 have a length sufficient to position the barb 127 near the distal end 120 of the inner cutting tube 102.

Figure 5D:
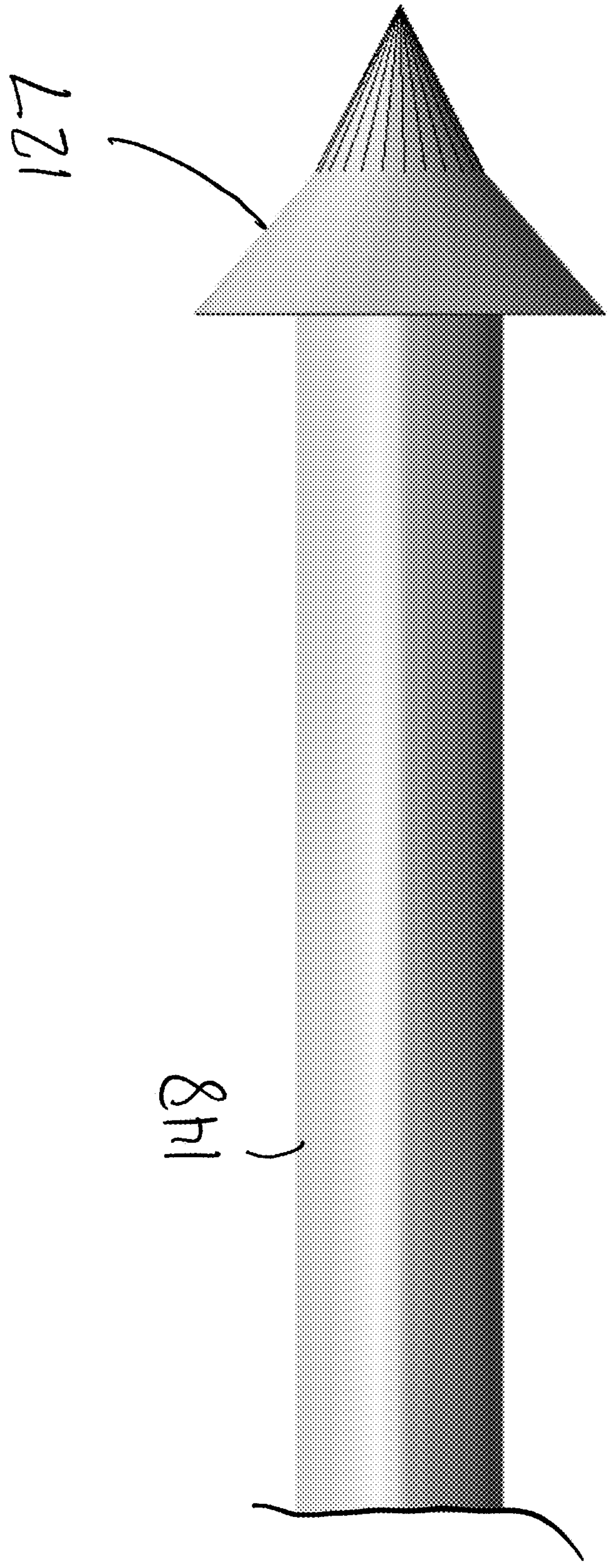
FIG. 5D is a detail view of the distal probe of the device of FIG. 5A.

The barb 127 of the probe 125 can include a maximum outer diameter that is sized to be received within the inner diameter of the inner cutting tube 102 so that upon distal extension of the inner cutting tube 102, the barb 127 enters at least partially inside the lumen 122. The geometry of the barb 127 is configured to retain the tissue slug 18 on the barb 127 even upon axial extension of the inner cutting tube 102 over the barb 127. For example, the barb 127 can be shaped like an arrowhead having one or more bladed wings that are designed to cut and penetrate tissue in a first direction and snag on the tissue in a second, opposite direction. The barb 127 can have a triangular or square-based pyramidal shape (see FIG. 5D).

During initial penetration of the trabecular meshwork 10, the probe 125 can be positioned so that the barb 127 extends distal to the distal end 120 of the inner cutting tube 102 (see FIGS. 7 and 8A). This allows for the barb 127 to penetrate the trabecular meshwork 10 prior to the inner cutting tube 102 penetrating the trabecular meshwork 10. Once the barb 127 is positioned within Schlemm's canal 12, the inner cutting tube 102 can be axially extended over the proximal shaft 129 and the barb 127 so that the distal end 120 of the inner cutting tube 102 shears the tissue positioned between the proximal-facing surface of the barb 127 and the distal end 120 of the inner cutting tube 102 creating a tissue slug 18 (see FIG. 8B). As the inner cutting tube 102 is used to create additional holes in the trabecular meshwork, each tissue slug 18 can stack up on the distal shaft 148 of the probe 125 proximal to the barb 127.

The thickness of the trabecular meshwork can vary between patients, but is generally between about 50-150 microns. Thus, the distal travel of the inner cutting tube 102 can be limited to at least 50 microns, but generally less than about 350 microns to avoid penetrating the outer wall of Schlemm's canal 12 during axial extension of the inner cutting tube 102. The geometry of the ridges 132 on the spindle 103 relative to the chamber 119 define the distal travel of the inner cutting tube 102. For example, the depth of the space between ridges 134 in the chamber 119 and/or the height of the ridges 132 on the distal-facing surface of the spindle 103 can determine the distal travel of the inner cutting tube 102. The depth of the space between the ridges 134 and the height of ridges 132 can be at least about 50 microns so that interdigitation of the ridges 132, 134 achieves a distal travel of at least about 50 microns.

In other implementations, the depth achieved by axial motion of the inner cutting tube 102 can be set by a user. In one implementation, the distal-facing surface of the stopper tube 115 can form a shoulder on a distal end region of the device 100. The shoulder is sized to abut against the trabecular meshwork surrounding the location of the penetration by the barb 127 and the inner cutting tube 102 and prevent over-insertion of the inner cutting tube 102 through the trabecular meshwork 10 so as to prevent damage to the outer wall of Schlemm's canal 12. The distal-facing surface of the stopper tube 115 can be arranged a known distance relative to the inner cutting tube 102 when in the fully extended position thereby limiting the depth of penetration achieved by the inner cutting tube 102. The depth of penetration of the inner cutting tube 102 can be between about 50 microns up to about 350 microns in a distal direction along the longitudinal axis and beyond the distal-facing surface of the stopper tube 115. The position of the stopper tube 115 relative to the outer housing 101 can be adjusted by a user to select the desired depth of penetration achieved by the inner cutting tube 102. The stopper tube 115 can be adjustably coupled to the outer housing 101 to modify the effective extension of the inner cutting tube 102. When the stopper tube 115 is adjusted to increase the distance of the distal-facing surface of the stopper tube 115 relative to the housing 101, the extension of the inner cutting tube 102 is decreased. When the stopper tube 115 is adjusted to decrease the distance of the distal-facing surface of the stopper tube 115 relative to the housing 101, the extension of the inner cutting tube 102 is increased. The adjustably coupling between the stopper tube 115 and the housing 101 can vary. In some implementations, the proximal end of the stopper tube 115 is in threaded engagement with a distal end of the housing 101 so that the relative distance between the distal-facing surface of the stopper tube 115 to the housing 101 is increased or decreased. In other implementations, the proximal end of the stopper tube 115 can be engaged with a component contained within the housing 101 to adjust the relative distance. Any of a variety of mechanical adjustments is considered herein to achieve a selected depth of penetration of the inner cutting tube 102 beyond the distal-facing surface of the stopper tube 115.

In other implementations, the distal travel of the inner cutting tube 102 can be great enough beyond the outer tube 115 to modulate tissue of the outer wall of Schlemm's canal 12. The axial travel can be uninhibited or the depth of penetration can be set so as to allow penetration of the outer wall, if desired. The outer tube 115 and the inner cutting tube 102 can each be straight so that motion in the distal direction is along the longitudinal axis A so as to penetrate the trabecular meshwork without traveling along the canal such as at an angle that causes the inner cutting tube 102 to cannulate the canal.

Simple punctures of the trabecular meshwork tend to heal over time so that the opening through the trabecular meshwork closes up. The devices described herein by virtue of the shearing action between the inner cutting tube 102 and the distal barb 127 removes cores from the trabecular meshwork that can be, for example, about 100-400 microns in diameter or just below the OD of the cutter tube 102. The cored trabecular meshwork is less likely to reclose following removal of the cutting tube 102 needs no stent or device designed to prop open the penetration due to the size of the opening.

In some implementations, a distal end region of the inner cutting tube 102 can be coated with at least one drug to provide a pharmacological effect at the site of tissue coring. For example, the distal end region of the inner cutting tube 102 that penetrates through the trabecular meshwork can be coated with a drug that reduces fibrotic and/or inflammatory tissue response to minimize or inhibit tissue healing following coring of the trabecular meshwork. The exposure of the tissue to the drug(s) can prevent healing maintaining the opening for a longer period of time after treatment with the device 100. The distal end region of the inner cutting tube 102 that is coated with the drug can be enclosed within the outer stopper tube 115 during insertion of the elongate shaft 110 into the eye and may only come into contact with eye tissue upon actuation of the device 100 and penetration of the trabecular meshwork with the inner cutting tube 102. The drug coating can vary including anti-cancer agents such as one or more of 5-fluorouracil, adriamycin, asparaginase, azacitidine, azathioprine, bleomycin, busulfan, carboplatin, carmustine, chlorambucil, cisplatin, cyclophosphamide, cyclosporine, cytarabine, dacarbazine, dactinomycin, daunorubicin, doxorubicin, estramustine, etoposide, etretinate, filgrastin, floxuridine, fludarabine, fluorouracil, fluoxymesterone, flutamide, goserelin, hydroxyurca, ifosfamide, leuprolide, levamisole, lomustine, nitrogen mustard, melphalan, mercaptopurine, methotrexate, mitomycin, mitotane, pentostatin, pipobroman, plicamycin, procarbazine, sargramostin, streptozocin, tamoxifen, taxol, teniposide, thioguanine, uracil mustard, vinblastine, vincristine and vindesine. The distal end region of the inner cutting tube 102 also can be coated with one or more materials such as a hydrophilic polymer coating to improve penetration of the tube 102 through the trabecular meshwork.

The device 100 can include a connection that is configured to receive tubing for supply of irrigation fluid to the eye during use. The irrigation fluid such as balanced saline solution (BSS) can be supplied from an external source through tubing connected to device 100 such as via an irrigation sleeve (not shown). The irrigation sleeve can be positioned over the elongate shaft 110 to provide irrigation fluid from an irrigation line through one or more irrigation openings in the sleeve that are positioned within the eye during use of the device. The irrigation fluid may also be coupled to the device in a manner that allowed the irrigation fluid to travel into the annular space 152 between the external surface of the cutting tube 102 and the internal surface of the outer tube 115 (see FIG. 2C). The fluid can be delivered using passive hydrostatic pressure from an irrigation bag hung at a head height. As mentioned above, the device 100 can incorporate a pair of thrust bearings including a distal thrust bearing **108*a* and a proximal thrust bearing 108*b*. The distal thrust bearing 108*a* can incorporate one or more features 130 that allow for fluid flow past the distal thrust bearing 108*a*. For example, the features 130 can be openings, slots, or channels formed in the distal thrust bearing 108*a* that prevent sealing between the distal thrust bearing 108*a* and the inner surface of the housing 101 such that fluid from the luer 109 can travel around the distal thrust bearing 108*a* and out the annular space between the inner cutting tube 102 and the outer tube 115. The proximal thrust bearing 108*b*, in contrast, has no features 130 (e.g., openings, slots, channels) that allow for fluid flow past the proximal thrust bearing 108*b*** where it engages the housing. The irrigation fluid can be used to prime the device prior to use.

The device 100 can incorporate one or more lights sources for visualization and/or targeting and/or photobiomodulation through the distal elongate shaft 110. The light source can be attached to the distal tip of the cutting tube 102. For example, one or more LEDs or laser diodes and corresponding fiber optics can be incorporated within the device to perform photobiomodulation including red (600-700 nm), near-infrared (770-1200 nm), white, blue, green, ultraviolet or near ultraviolet, or other colors. The light source can be a laser light source in the spectrum of 630 nm to 670 nm in order to ablate the tissue. The laser light ablation can be in addition to the mechanical punch by the cutting tube 102 or in lieu of the mechanical punch. For example, the laser light can ablate the tissue slug created by the mechanical punch. The laser light itself can ablate the tissue at the end of the distal cutting tube 102 so that no slug is created that need be removed through the lumen 122. In some implementations, an endoscopic surgical tool having one or more lenses, image sensors, or other sensor that is able to be coupled to the device 100 for the purpose of visualization during the procedure.

Power can be supplied to the device 100 such as via the cable extending from a proximal end of the housing 101. The cable may also be configured to connect the device 100 to a wall socket. The device 100 can also be powered by one or more internal batteries. The battery can be incorporated within a region of the device 100, either internally or coupled to a region of the housing such as within a modular, removable battery pack. The battery can have different chemical compositions or characteristics. For instance, batteries can include lead-acid, nickel cadmium, nickel metal hydride, silver-oxide, mercury oxide, lithium ion, lithium ion polymer, or other lithium chemistries. The device can also include rechargeable batteries using either a DC power-port, induction, solar cells, or the like for recharging. Power systems known in the art for powering medical devices for use in the operating room are also to be considered herein such as spring power or any other suitable internal or external power source.

The device is designed to be single-use disposable device. The device can be formed of a metal and/or polymer material.

As an example method of use, the eye can be penetrated by the distal end 120 of the cutting tube 102. An incision (e.g., 1.5-2.2 mm long) may be created using a cutting tool for clear corneal incisions or a puncture tool and the sulcus can be deepened using ophthalmic viscoelastic. The distal end region of the elongate shaft 110 can be inserted into and advanced through the anterior chamber 16 towards the target intraocular tissue such as the trabecular meshwork 10 or an inner wall of Schlemm's canal 12. There are various ways to approach the trabecular meshwork 10 and many techniques that can be employed depending on lens status, type and severity of the disease being treated.

The distal probe 125 can be positioned relative to the elongate shaft 110 so that the barb 127 forms a distal-most end of the device to it can be used to initially penetrate the trabecular meshwork 10 and be positioned within Schlemm's canal 12. The barb 127 can be advanced into Schlemm's canal 12 by applying a force with the device 100 against the eye. Alternatively, the barb 127 can be advanced distally relative to the housing 101 in order to penetrate the target tissue in the eye. The force can be a linearly applied force in a distal direction that is configured to cause the barb 127 to penetrate the trabecular meshwork 10. The distal-facing surface of the stopper tube 115 can abut against the trabecular meshwork 10 and the distal end 120 of the cutting tube 102 can be fully sheathed by the outer stopper tube 115 so that both remain outside Schlemm's canal 12 while the barb 127 is positioned inside Schlemm's canal 12. Upon actuation of the device 100 such as by pressing trigger 105, the cutting tube 102 rotates while advancing distally beyond the distal-facing surface of the stopper tube 115 abutting against the trabecular meshwork to penetrate through the trabecular meshwork 10 towards the proximal-facing surface of the barb 127 positioned inside Schlemm's canal 12. The axial motion of the rotating distal end 120 of the cutting tube 102 past the proximal-facing surface of the barb 127 shears the trabecular meshwork 10. The rotary forces and the axial forces combine to separate the tissue slug 18 from the trabecular meshwork 10. The tissue slug 18 created remains speared by the barb 127 now located within the lumen 122 of the cutting tube 102 so that it can be removed from the eye. Vacuum generated by relative movement between the rotary housing 104 and the rotary spindle 103 is exposed to the lumen 122 of the cutting tube 102 to aid in retaining the tissue slug 18 within the lumen 122 as the mechanical punch occurs.

Perforation of the trabecular meshwork 10 and/or an inner wall of Schlemm's canal 12 can be performed one or more times to create an opening between Schlemm's canal 12 and the anterior chamber 16 to drain aqueous humor into Schlemm's canal 12 more readily. Preferably more than a single core is created with the device. The surgeon may actuate the device 100 multiple times with a single winding of the torsion spring 107 to achieve at least 2, at least 3, at least 4, at least 5, at least 6, up to about 10-12 actuations of the cutting tube 102 before the device needs to be reset. The holes can be created 360 degrees around a circumference of the eye. The holes can be created around about 360 degrees through a single penetration of the eye. The elongate shaft 110 may be curved to achieve this range of access. The holes can be created around about 180 degrees through a first penetration of the eye and about 180 degrees through a second, different penetration of the eye. With each hole created, the tissue slug 18 can stack onto the distal shaft 148 of the probe 125 proximal to the barb 127.

The tissue slug(s) 18 can be removed by withdrawing the entire cutting tube 102 from the eye or by withdrawing the barb 127 from the cutting tube 102 towards a proximal end region of the housing 101. The tissue slug 18 can also be removed by applying aspiration through the device to draw it from the lumen of the cutting tube 102.

Use of the terms "hand piece" "hand-held" or "handle" herein need not be limited to a surgeon's hand and can include a hand piece coupled to a robotic arm or robotic system or other computer-assisted surgical system in which the user uses a computer console to manipulate the controls of the instrument. The computer can translate the user's movements and actuation of the controls to be then carried out on the patient by the robotic arm.

The system can include a control unit, power source, microprocessor computer, and the like. Aspects of the subject matter described herein may be realized in digital electronic circuitry, integrated circuitry, specially designed ASICs (application specific integrated circuits), computer hardware, firmware, software, and/or combinations thereof. These various implementations may include an implementation in one or more computer programs that are executable and/or interpretable on a programmable system including at least one programmable processor, which may be special or general purpose, coupled to receive signals, data and instructions from, and to transmit signals, data, and instructions to, a storage system, at least one input device, and at least one output device.

These computer programs (also known as programs, software, software applications, or code) include machine instructions for a programmable processor, and may be implemented in a high-level procedural and/or object-oriented programming language, and/or in assembly/machine language. As used herein, the term "machine-readable medium" refers to any computer program product, apparatus, and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

In various implementations, description is made with reference to the figures. However, certain implementations may be practiced without one or more of these specific details, or in combination with other known methods and configurations. In the description, numerous specific details are set forth, such as specific configurations, dimensions, and processes, in order to provide a thorough understanding of the implementations. In other instances, well-known processes and manufacturing techniques have not been described in particular detail in order to not unnecessarily obscure the description. Reference throughout this specification to "one embodiment," "an embodiment," "one implementation, "an implementation," or the like, means that a particular feature, structure, configuration, or characteristic described is included in at least one embodiment or implementation. Thus, the appearance of the phrase "one embodiment," "an embodiment," "one implementation, "an implementation," or the like, in various places throughout this specification are not necessarily referring to the same embodiment or implementation. Furthermore, the particular features, structures, configurations, or characteristics may be combined in any suitable manner in one or more implementations.

The use of relative terms throughout the description may denote a relative position or direction. For example, "distal" may indicate a first direction away from a reference point. Similarly, "proximal" may indicate a location in a second direction opposite to the first direction. The reference point used herein may be the operator such that the terms "proximal" and "distal" are in reference to an operator using the device. A region of the device that is closer to an operator may be described herein as "proximal" and a region of the device that is further away from an operator may be described herein as "distal". Similarly, the terms "proximal" and "distal" may also be used herein to refer to anatomical locations of a patient from the perspective of an operator or from the perspective of an entry point or along a path of insertion from the entry point of the system. As such, a location that is proximal may mean a location in the patient that is closer to an entry point of the device along a path of insertion towards a target and a location that is distal may mean a location in a patient that is further away from an entry point of the device along a path of insertion towards the target location. However, such terms are provided to establish relative frames of reference, and are not intended to limit the use or orientation of the devices to a specific configuration described in the various implementations.

As used herein, the term "about" means a range of values including the specified value, which a person of ordinary skill in the art would consider reasonably similar to the specified value. In aspects, about means within a standard deviation using measurements generally acceptable in the art. In aspects, about means a range extending to +/−10% of the specified value. In aspects, about includes the specified value.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

The systems disclosed herein may be packaged together in a single package. The finished package would be sterilized using sterilization methods such as Ethylene oxide or radiation and labeled and boxed. Instructions for use may also be provided in-box or through an internet link printed on the label.

All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claims. No language in the specification should be construed as indicating any non-claimed element essential to the practice of the invention.

What is claimed is:

1. A device to treat an ocular condition, the device comprising:

an outer housing having a proximal end region and a distal end region;

a rotary housing located within the outer housing rotationally fixed to a rotary spindle and rotationally movable relative to the outer housing;

an elongate shaft projecting distally from the distal end region of the outer housing along a central longitudinal axis, at least a distal end region of the elongate shaft being sized for insertion into an eye, wherein the elongate shaft comprises:

an outer shaft having a lumen; and an inner cutting tube positioned at least partially within the lumen of the outer shaft and movable relative to the outer shaft, a distal end of the inner cutting tube comprising a distal opening defined by a distal cutting surface, wherein a proximal end region of the inner cutting tube is fixedly coupled to the rotary spindle; and a distal probe having a proximal shaft extending within the inner cutting tube and a barb positioned on a distal end of the proximal shaft, wherein the distal cutting surface advances beyond the barb of the distal probe upon actuation of the device, wherein, upon actuation of the device, the rotary housing rotates causing the rotary spindle and the inner cutting tube to rotate around the central longitudinal axis while simultaneously causing axial extension of the inner cutting tube distally along the central longitudinal axis to advance the distal cutting surface through a target tissue forming a tissue slug.

2. The device of claim 1, wherein the proximal shaft has a length to position the barb distal to the distal end of the inner cutting tube so the barb penetrates the target tissue prior to penetration of the tissue by the inner cutting tube.

3. The device of claim 1, wherein the barb is sized to be received within a lumen of the inner cutting tube.

4. The device of claim 1, wherein the barb is shaped to penetrate and capture the tissue slug.

5. The device of claim 1, wherein the outer shaft is integral with or adjustably coupled to the outer housing.

6. The device of claim 1, wherein rotary motion of the rotary housing is achieved mechanically via a torsion spring.

7. The device of claim 6, wherein the torsion spring encircles a portion of the rotary housing and is configured to place the rotary housing under a torsional load.

8. The device of claim 7, wherein the device further comprises an actuator configured to initiate motion of the inner cutting tube.

9. The device of claim 8, wherein the actuator transforms potential energy of the torsion spring into rotational and axial motion of the inner cutting tube.

10. The device of claim 8, wherein the actuator is configured to engage at least a portion of the rotary housing, actuating the actuator releases engagement between the actuator and the rotary housing allowing free rotation of the rotary housing relative to the outer housing due to the torsional load applied by the torsion spring.

11. The device of claim 8, wherein the rotary housing incorporates a thread on an external surface of the rotary housing that is configured to engage a corresponding thread on an inner surface of the outer housing.

12. The device of claim 11, wherein rotation of the rotary housing translates into axial motion of the rotary housing due to engagement between the thread on the external surface and the corresponding thread on the inner surface.

13. The device of claim 6, wherein the torsion spring causes rotation of the rotary housing around the central longitudinal axis and axial motion of the rotary housing along the central longitudinal axis.

14. The device of claim 1, further comprising a vacuum source configured to apply a vacuum through the inner cutting tube.

15. The device of claim 14, wherein the vacuum source is an external vacuum source.

16. The device of claim 14, wherein the vacuum source is an internal vacuum source located within the outer housing.

17. The device of claim 16, wherein the internal vacuum source is a syringe mechanism comprising the rotary housing and the rotary spindle.

18. The device of claim 14, wherein axial motion of the rotary housing in a proximal direction relative to the rotary spindle creates the vacuum within the outer housing.

19. The device of claim 18, wherein the vacuum generated by the internal vacuum source is exposed to the inner cutting tube upon actuation of inner cutting tube motion.

20. The device of claim 14, wherein the vacuum is sufficient to draw the target tissue toward the distal end of the inner cutting tube during cutting the target tissue and without drawing the target tissue into the distal opening.

21. The device of claim 14, wherein the vacuum is sufficient to draw the tissue slug through at least a portion of the inner cutting tube.

22. The device of claim 1, wherein the inner cutting tube is configured to move axially by at least 50 microns up to about 350 microns.

23. The device of claim 1, wherein the rotary spindle is axially movable relative to the rotary housing and axially movable relative to the outer housing along the central longitudinal axis.

24. The device of claim 23, wherein a spring located within the outer housing is arranged to urge the rotary spindle in a distal direction within the outer housing.

25. The device of claim 24, wherein the rotary spindle comprises a plurality of ridges on a distal-facing surface configured to mate with a corresponding plurality of ridges within the outer housing urging the rotary spindle in a proximal direction and compressing the spring located within the outer housing.

26. The device of claim 25, wherein interdigitation of the plurality of ridges on the distal-facing surface with the corresponding plurality of ridges within the outer housing causes distal extension of the inner cutting tube as the spring urges the rotary spindle in a distal direction relative to the outer housing.

27. A device to treat an ocular condition, the device comprising:

an outer housing having a proximal end region and a distal end region;

a rotary housing located within the outer housing rotationally fixed to a rotary spindle and rotationally movable relative to the outer housing;

an elongate shaft projecting distally from the distal end region of the outer housing along a central longitudinal axis, at least a distal end region of the elongate shaft being sized for insertion into an eye, wherein the elongate shaft comprises:

an outer shaft having a lumen; and an inner cutting tube positioned at least partially within the lumen of the outer shaft and movable relative to the outer shaft, a distal end of the inner cutting tube comprising a distal opening defined by a distal cutting surface, wherein a proximal end region of the inner cutting tube is fixedly coupled to the rotary spindle; and wherein, upon actuation of the device, the rotary housing rotates causing the rotary spindle and the inner cutting tube to rotate around the central longitudinal axis while simultaneously causing axial extension of the inner cutting tube distally along the central longitudinal axis to advance the distal cutting surface through a target tissue forming a tissue slug, wherein rotary motion of the rotary housing is achieved mechanically via a torsion spring.

28. A device to treat an ocular condition, the device comprising:

an outer housing having a proximal end region and a distal end region;

a rotary housing located within the outer housing rotationally fixed to a rotary spindle and rotationally movable relative to the outer housing;

an elongate shaft projecting distally from the distal end region of the outer housing along a central longitudinal axis, at least a distal end region of the elongate shaft being sized for insertion into an eye, wherein the elongate shaft comprises:

an outer shaft having a lumen; and an inner cutting tube positioned at least partially within the lumen of the outer shaft and movable relative to the outer shaft, a distal end of the inner cutting tube comprising a distal opening defined by a distal cutting surface, wherein a proximal end region of the inner cutting tube is fixedly coupled to the rotary spindle; and a vacuum source configured to apply a vacuum through the inner cutting tube, wherein, upon actuation of the device, the rotary housing rotates causing the rotary spindle and the inner cutting tube to rotate around the central longitudinal axis while simultaneously causing axial extension of the inner cutting tube distally along the central longitudinal axis to advance the distal cutting surface through a target tissue forming a tissue slug, wherein axial motion of the rotary housing in a proximal direction relative to the rotary spindle creates the vacuum within the outer housing.

* * * * *